US008337854B2

(12) United States Patent
Goncalvez et al.

(10) Patent No.: US 8,337,854 B2
(45) Date of Patent: Dec. 25, 2012

(54) MONOCLONAL ANTIBODIES AGAINST DENGUE AND OTHER VIRUSES WITH DELETION IN FC REGION

(75) Inventors: Ana P. Goncalvez, Rockville, MD (US); Robert H. Purcell, Gaithersburg, MD (US); Ching-Juh Lai, Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 315 days.

(21) Appl. No.: 12/594,756

(22) PCT Filed: Apr. 3, 2008

(86) PCT No.: PCT/US2008/059313
§ 371 (c)(1),
(2), (4) Date: Jun. 1, 2010

(87) PCT Pub. No.: WO2009/011941
PCT Pub. Date: Jan. 22, 2009

(65) Prior Publication Data
US 2010/0247549 A1 Sep. 30, 2010

Related U.S. Application Data

(60) Provisional application No. 60/922,282, filed on Apr. 4, 2007, provisional application No. 60/927,755, filed on May 4, 2007, provisional application No. 60/928,405, filed on May 8, 2007.

(51) Int. Cl.
*A61K 39/42* (2006.01)
*A61K 39/12* (2006.01)
*C12Q 1/70* (2006.01)
(52) U.S. Cl. ............... 424/159.1; 424/218.1; 435/5
(58) Field of Classification Search ............... None
See application file for complete search history.

(56) References Cited

U.S. PATENT DOCUMENTS
7,622,113 B2 * 11/2009 Lai et al. .............. 424/133.1

FOREIGN PATENT DOCUMENTS
WO    WO-2005/056600 A2    6/2005

OTHER PUBLICATIONS

Men et al., Journal of Virology, May 2004, 78(9):4665-4674.*
Chappel et al., "Identification of the Fcγ Receptor Class I Binding Site in Human IgG Through the Use of Recombinant IgG1/IgG2 Hybrid and Point-Mutated Antibodies", Proc. Natl. Acad. Sci. USA, vol. 88, No. 20, pp. 9036-9040 (1991).
Lai et al., "Epitope Determinants of a Chimpanzee Dengue Virus Type 4 (DENV-4)-Neutralizing Antibody and Protection Against DENV-4 Challenge in Mice and Rhesus Monkeys by Passively Transferred Humanized Antibody", Journal of Virology, vol. 81, No. 23, pp. 12766-12774 (2007).
Goncalves et al., "Monoclonal Antibody-Mediated Enhancement of Dengue Virus Infection in Vitro and in Vivo and Strategies for Prevention", Proc. Natl. Acad. Sci. USA, vol. 104, No. 22, pp. 9422-9427 (2007).
Mady et al., "Neuraminidase Augments Fcγ Receptor II-Mediated Antibody-Dependent Enhancement of Dengue Virus Infection", Journal of General Virology, vol. 74, pp. 839-844 (1993).
Canfield et al., "The Binding Affinity of Human IgG for its High Affinity Fc Receptor is Determined by Multiple Amino Acids in the CH2 Domain and is Modulated by the Hinge Region", J. Exp. Med., vol. 173, No. 6, pp. 1483-1491 (1991).
Medgyesi et al., "Functional Mapping of the FcγRII Binding Site on Human IgG1 by Synthetic Peptides", Eur. J. Immunol., vol. 34, No. 4, pp. 1127-1135 (2004).

* cited by examiner

*Primary Examiner* — Stacy B. Chen
(74) *Attorney, Agent, or Firm* — Edwards Wildman Palmer LLP; Peter F. Corless

(57) ABSTRACT

The present invention relates to a variant of a parent polypeptide comprising an Fc region, which variant binds an Fc gamma receptor (FcγR) with lower affinity than the parent polypeptide and comprises a deletion of at least one amino acid in about position 100 to about position 150 in the Fc region and related nucleic acids, vectors, host cells and methods of producing the variant and methods for preventing or treating a disorder in a mammal.

16 Claims, 14 Drawing Sheets

```
                    G₀      H₀
                    174▼   176▼
SEQ ID NO:
    41      DEN4 wt  SHSRKIED VETHIC
    42      DEN4 v3  ......E.../........
    43      DEN4 v4  .......L..........
    44      DEN3     ASIAAI.E..TGE
    45      DEN2     SITAE.TG..TVME
    46      DEN1     AHS.IQ.T..A....
    47      JEV      A..IIL.G...V....
    48      WN       A..VIL.G...V....
    49      TBEV     IKHTMEG..DSL.
    50      YFV      GQ.EHG..KA.E
```

MONOCLONAL ANTIBODIES AGAINST DENGUE AND OTHER VIRUSES WITH DELETION IN FC REGION

FIELD OF THE INVENTION

Aspects of the present invention relate to immunology. More specifically, some embodiments include polypeptides comprising deletions in the Fc region and the use of these compositions for the treatment and prevention of disease.

REFERENCE TO SEQUENCE LISTING, TABLE, OR COMPUTER PROGRAM LISTING

The present application is being filed along with a Sequence Listing in electronic format. The Sequence Listing is provided as a file entitled NIH355.001VPC.txt, created Apr. 1, 2008, which is 31 Kb in size. The information in the electronic format of the Sequence Listing is incorporated herein by reference in its entirety.

DESCRIPTION OF THE RELATED ART

The four dengue virus serotypes (DENV-1 to DENV-4) are extremely important arthropod-borne flaviviruses in terms of morbidity and geographic distribution. Up to 100 million DENV infections occur every year, mostly in tropical and subtropical areas where vector mosquitos are abundant (Monath, T. P. 1994 *Proc Natl Acad Sci USA* 91:2395-2400). Infection with any of the DENV may be asymptomatic or may lead to classic dengue fever or more severe dengue hemorrhagic fever (DHF) and dengue shock syndrome (DSS), which are increasingly common in the dengue endemic areas. Immunity to the same virus serotype (homotypic immunity) is life-long; whereas immunity to different serotypes (heterotypic immunity) lasts 2-3 months so that infection with a different serotype virus is possible (Sabin, A. B. 1952 *Am J Trop Med Hyg* 1:30-50). DHF/DSS often occurs in patients with second, heterotypic DENV infections or in infants with maternally transferred dengue immunity (Halstead, S. B. 1970 *Yale J Biol Med* 42:350-362; Kliks, S. C. et al. 1988 *Am J Trop Med Hyg* 38:411-419). Severe dengue is a major cause of hospitalization and has a high fatality rate, especially in children.

Antibody-dependent enhancement (ADE) has been proposed as an underlying pathogenic mechanism of DHF/DSS (Halstead, S. B. 1970 *Yale J Biol Med* 42:350-362). ADE occurs because pre-existing sub-neutralizing antibodies and the infecting DENV form complexes that bind to Fc receptor (Fc R)-bearing cells, leading to increased virus uptake and replication (Kliks, S. C. et al. 1988 *Am J Trop Med Hyg* 38:411-419). ADE has been repeatedly demonstrated in vitro using dengue immune sera or monoclonal antibodies and cells of monocytic and recently, B lymphocytic lineages bearing Fc receptors (Littaua, R. et al. 1990 *J Immunol* 144:3183-3186; Morens, D. M. et al. 1987 *J Gen Virol* 68:91-98; Lin, Y. W. et al. 2002 *J Virol* 76:12242-12249). ADE of DENV-2 infection has also been demonstrated in monkeys infused with a human dengue immune serum (Halstead, S. B. 1979 *J Infect Dis* 140:527-533).

Infection with DENV or any other flavivirus induces broadly cross-reactive, but weak- or non-neutralizing antibodies (Heinz, F. X. 1986 *Adv Virus Res* 31: 103-168; Roehrig, J. T. et al. 1998 *Virology* 246:317-328). These antibodies remain detectable for a long period and rise rapidly during a subsequent heterotypic infection as a result of an anamnestic response. A major subset of these cross-reactive antibodies is directed to immuno-dominant epitopes involving determinants mapped to the flavivirus-conserved fusion peptide in the envelope glycoprotein (E) (Goncalvez, A. P. et al. 2004 *J Virol* 78:12919-12928; Oliphant, T. et al. 2006 *J Virol* 80:12149-12159; Stiasny, K. et al. 2006 *J Virol* 80:9557-9568). The functional activities of these cross-reactive antibodies are not well characterized.

Chimpanzee-human chimeric IgG1 MAbs capable of neutralizing or binding to one or more DENV serotypes were identified (Goncalvez, A. P. et al. 2004 *J Virol* 78:12910-12918; Men, R. et al. 2004 *J Virol* 78:4665-4674). Among these humanized antibodies, cross-reactive IgG 1A5 neutralizes DENV-1 and DENV-2 more efficiently than DENV-3 and DENV-4. Analysis of antigenic variants has localized the IgG 1A5 binding site to the conserved fusion peptide in E (Goncalvez, A. P. et al. 2004 *J Virol* 78:12919-12928). Thus, IgG 1A5 shares many characteristics with the cross-reactive antibodies detected in flavivirus infections.

SUMMARY OF THE INVENTION

The ability of IgG 1A5 to mediate enhancement of DENV replication in monocyte-derived cell lines and in juvenile rhesus monkeys following passive transfer was investigated. Strategies to reduce antibody-dependent enhancement (ADE) by mutational analysis of the key structures in the Fc of IgG 1A5 were also explored. A 9-amino-acid deletion at the N-terminus of Fc was identified as responsible for complete abrogation of DENV ADE in vitro. These findings have implications for DENV pathogenesis, as well as, for antibody-mediated prevention of dengue. In addition, the epitope determinants of a DENV-4-specific MAb were determined by isolation and sequence analysis of antigenic variants. Protection against DENV-4 challenge was demonstrated in mice and rhesus monkeys by passively transferred humanized antibody. Furthermore, the effect of the 9-amino acid deletion in the antibody Fc region on the functional activity and stability of MAb 5H2 in chimpanzees was evaluated.

Embodiments disclosed herein relate to a composition comprising a peptide of SEQ ID NO: 51 or SEQ ID NO: 52, wherein the peptide comprises a deletion of at least 1 amino acid in about position 100 to about position 150. In some embodiments, the peptide comprises a deletion of at least about 4 amino acids. In other embodiments, the peptide comprises a deletion of at least about 9 amino acids.

In some embodiments, the peptide binds an Fc gamma receptor (FcγR) with lower affinity than a peptide of SEQ ID NO: 53 or 54. In some embodiments, the peptide has about 100 fold lower affinity to the Fc gamma receptor (FcγR) than SEQ ID NO: 53 or 54.

In some embodiments, the deletion is from about position 114 to about position 122. In some embodiments the deletion is APELLGGPS (SEQ ID NO: 16).

In other embodiments, the peptide is not 5H2.

In some embodiments, the composition can be an antibody or fragment thereof.

Other embodiments relate to a composition comprising a nucleic acid encoding a peptide of SEQ ID NO: 51 or SEQ ID NO: 52, wherein the peptide comprises a deletion of at least 1 amino acid in about position 100 to about position 150. In some embodiments, the nucleic acid encodes a peptide that comprises a deletion of at least about 4 amino acids. In other embodiments, the nucleic acid encodes a peptide that comprises a deletion of at least about 9 amino acids. In some embodiments, the nucleic acid encodes a peptide that binds an Fc gamma receptor (FcγR) with lower affinity than a peptide of SEQ ID NO: 53 or 54. In some embodiments, the nucleic acid encodes a peptide that has about 100 fold lower affinity to the Fc gamma receptor (FcγR) than SEQ ID NO: 53 or 54. In some embodiments, the deletion is from about position 114 to about position 122. In some embodiments the deletion is APELLGGPS (SEQ ID NO: 16). In some embodiments, the nucleic acid encodes a peptide that is not 5H2.

Other embodiments relate to a vector comprising the nucleic acid of the peptide of embodiments disclosed herein. Further embodiments relate to a host cell comprising the vector of embodiments disclosed herein.

Additional embodiments relate to a method for preventing or treating dengue virus infection or a symptom thereof in a mammal including providing to the mammal a prophylactically or therapeutically effective amount of the composition of any of the embodiments disclosed herein. This method can involve identifying a mammal in need of an agent that prevents or treats dengue virus infection or a symptom thereof. The identification can be by clinical evaluation or evaluation by diagnostic approach. Some embodiments relate to measuring a marker of dengue virus infection or a symptom thereof in said mammal. The measurement can be a measurement of viral load in the mammal.

More embodiments relate to a method of reducing antibody-dependent enhancement (ADE) in a mammal including providing to the mammal a composition of any of the embodiments disclosed herein. This method can involve identifying a mammal in need of an agent that reduces antibody-dependent enhancement (ADE). The identification can be by clinical evaluation or evaluation by diagnostic approach. Some embodiments relate to measuring a marker of antibody-dependent enhancement (ADE). The measurement can be a measurement of viral load in the mammal.

Yet further embodiments relate to a method of inducing a complement-mediated neutralization in a mammal including providing to the mammal a composition of any of the embodiments disclosed herein. This method can involve identifying a mammal in need of an agent that induces a complement-mediated neutralization. The identification can be by clinical evaluation or evaluation by diagnostic approach. Some embodiments relate to measuring a marker of complement-mediated neutralization. The measurement can be a measurement of viral load in the mammal.

Other embodiments relate to a method of inducing antibody-dependent cellular toxicity in a mammal including providing to the mammal a composition of any of the embodiments disclosed herein. This method can involve identifying a mammal in need of an agent that induces an antibody-dependent cellular toxicity. The identification can be by clinical evaluation or evaluation by diagnostic approach. Some embodiments relate to measuring a marker of antibody-dependent cellular toxicity. The measurement can be a measurement of viral load in the mammal.

BRIEF DESCRIPTION OF THE DRAWINGS

FIG. 8. Comparison of amino acid sequences of E protein of wild type DENV-4, antigenic variants and other flaviviruses (A). In the sequence alignment, a dot indicates an identical amino acid when compared with compared with DENV-4. Localization of amino acid substitutions at positions 174 and 176 in the 3-D structure of monomeric DENV-2 E viewed from the top (B) and from the side (C). Domain I is in red, domain II in yellow, and domain III in blue.

PUBLICATION AND DEPOSIT OF BIOLOGICAL MATERIAL

Figure 1:
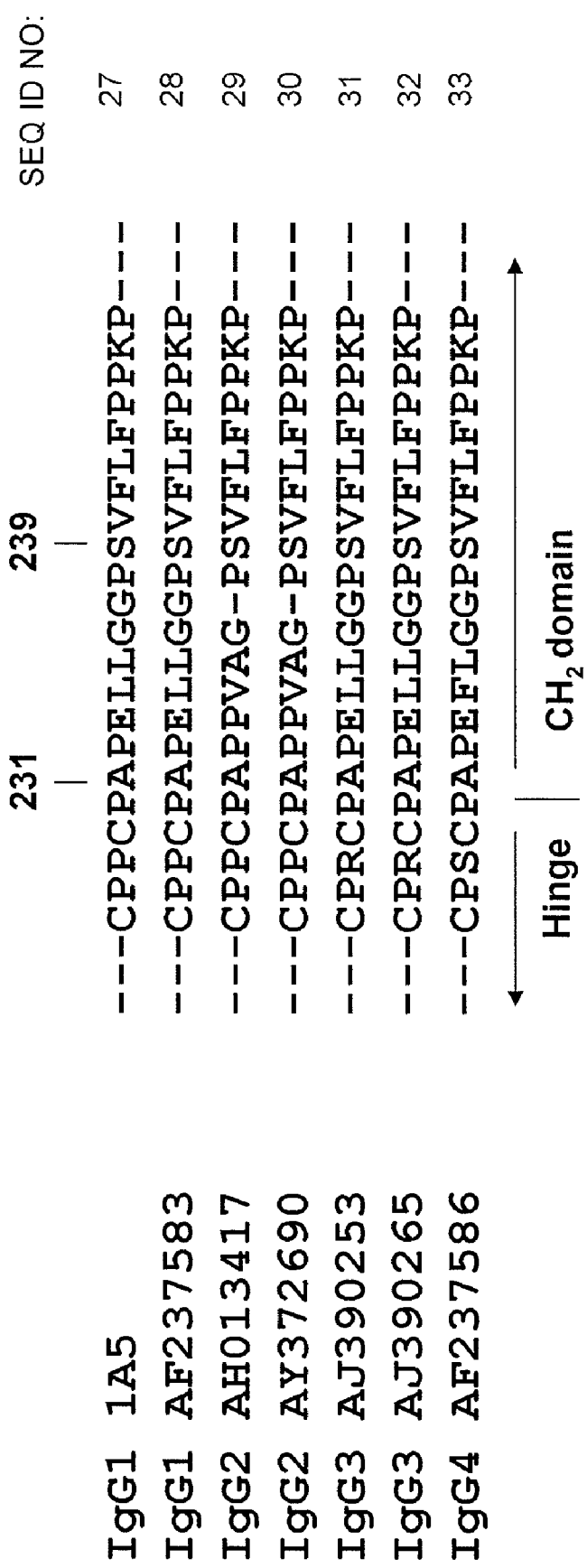
FIG. 1. Alignment of IgG subtype sequences surrounding the 9-amino acid deletion region.

The 1A5 and 5H2 biological material has been published as Goncalvez, A. P. et al. 2004 *J Virol* 78:12910-12918 and Men, R. et al. 2004 *J Virol* 78:4665-4674. Additionally, the 1A5 and 5H2 biological material has been deposited in accordance with the terms of the Budapest Treaty with the American Type Culture Collection (ATCC), Manassas, Va., on the dates indicated:

| Biological Material | Designation No. | Date |
|---|---|---|
| Plasmid: Humanized IgG1 5H2 | PTA-5662 | Nov. 26, 2003 |
| Plasmid: Humanized IgG1 1A5 | PTA-6265 | Oct. 22, 2004 |

DETAILED DESCRIPTION OF THE PREFERRED EMBODIMENT

The ability of IgG 1A5 to mediate enhancement of DENV replication in monocyte-derived cell lines and in juvenile rhesus monkeys following passive transfer was investigated. Strategies to reduce ADE by mutational analysis of the key structures in the Fc of IgG 1A5 were also explored. A 9-amino-acid deletion at the N-terminus of Fc was identified as responsible for complete abrogation of DENV ADE in vitro. These findings have implications for DENV pathogenesis, as well as, for antibody-mediated prevention of dengue. In addition, the epitope determinants of a DENV-4-specific MAb were determined by isolation and sequence analysis of antigenic variants. Protection against DENV-4 challenge was demonstrated in mice and rhesus monkeys by passively transferred humanized antibody. Furthermore, the effect of the 9-amino acid deletion in the antibody Fc region on the functional activity and stability of MAb 5H2 in chimpanzees was evaluated.

Unless defined otherwise, technical and scientific terms used herein have the same meaning as commonly understood by one of ordinary skill in the art to which this invention belongs. See, e.g., Singleton P and Sainsbury D., in *Dictionary of Microbiology and Molecular Biology* 3rd ed., J. Wiley & Sons, Chichester, N.Y., 2001.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody.

A "parent polypeptide" is a polypeptide comprising an amino acid sequence that lacks one or more of the Fc region modifications disclosed herein and that differs in effector function compared to a polypeptide variant as herein disclosed. The parent polypeptide may comprise a native sequence Fc region or an Fc region with pre-existing amino acid sequence modifications (such as additions, deletions and/or substitutions).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, $C_H2$ and $C_H3$.

The "$C_H2$ domain" of a human IgG Fc region (also referred to as "Cγ2" domain) usually extends from about amino acid 231 to about amino acid 340. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the $C_H2$ domain.

The "$C_H3$ domain" comprises the stretch of residues C-terminal to a $C_H2$ domain in an Fc region (i.e., from about amino acid residue 341 to about amino acid residue 447 of an IgG).

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof.

A "variant Fc region" comprises an amino acid sequence that differs from that of a native sequence Fc region by virtue of at least one "amino acid modification" as herein defined. Preferably, the variant Fc region has at least one amino acid modification compared to a native sequence Fc region or to the Fc region of a parent polypeptide, e.g., from about one to about ten amino acid modifications in a native sequence Fc region or in the Fc region of the parent polypeptide. Embodiments disclosed herein include variant Fc regions that can have the following degrees of amino acid sequence homology or identity to the Fc region of a parent polypeptide, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate variant Fc regions having greater than or equal to 35% homology or identity can be identified by methods known in the art and can be subsequently examined using functional assays, for example, the assays described herein and those known in the art. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "ClustalW, which is available, for example, on the world-wide web at ebi.ac.uk/clustalw.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. Other FcRs, including those to be identified in the future, are encompassed by the term "FcR" herein. The term also includes the neonatal receptor, FcRn, which is responsible for the transfer of maternal IgGs to the fetus. The term includes allotypes, such as FcγRIIIA allotypes: FcγRIIIA-Phe$_{158}$, FcγRIIIA-Val$_{158}$, FcγRIIA-R$_{131}$ and/or FcγRIIA-H$_{131}$.

"Human effector cells" are leukocytes that express one or more FcRs and perform effector functions.

A polypeptide variant with "altered" FcR binding affinity is one that has diminished FcR binding activity compared to a parent polypeptide or to a polypeptide comprising a native sequence Fc region. The polypeptide variant that "displays decreased binding" to an FcR binds at least one FcR with worse affinity than a parent polypeptide. The decrease in binding compared to a parent polypeptide may be about 40% or more decrease in binding, e.g., down to a variant that possesses little or no appreciable binding to the FcR. Such variants that display decreased binding to an FcR may possess little or no appreciable binding to an FcR, e.g., 0-20% binding to the FcR compared to a native sequence IgG Fc region.

An "amino acid modification" refers to a change in the amino acid sequence of a predetermined amino acid sequence. Exemplary modifications include an amino acid substitutions, insertions and/or deletions. The preferred amino acid modification herein is a deletion.

An "amino acid modification at" a specified position, e.g., of the Fc region, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Leu): leucine (Leu); lysine (Lys); methionine (Met); phenylalanine (Phe); proline (Pro); serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues.

An "amino acid insertion" refers to the incorporation of at least one amino acid into a predetermined amino acid sequence.

An "amino acid deletion" refers to the removal of at least one amino acid residue from a predetermined amino acid sequence.

"Hinge region" is generally defined as stretching from Glu216 to Pro230 of human IgG1. Hinge regions of other IgG isotypes may be aligned with the IgG1 sequence by placing the first and last cysteine residues forming inter-heavy chain S—S bonds in the same positions.

The term "binding domain" refers to the region of a polypeptide that binds to another molecule. In the case of an FcR, the binding domain can comprise a portion of a polypeptide chain thereof (e.g., the α chain thereof) that is responsible for binding an Fc region. One useful binding domain is the extracellular domain of an FcR α chain.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined for the purpose of the present invention, comprise a portion of an intact antibody, generally including the antigen binding or variable region of the intact antibody and the Fc region of an antibody that retains FcR binding capability. Examples of antibody fragments include linear antibodies; single-chain antibody molecules; and multispecific antibodies formed from antibody fragments. The antibody fragments preferably retain at least part of the hinge and optionally the $C_H1$ region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein 1975 Nature 256:495, or may be made by recombinant DNA methods. The "monoclonal antibodies" may also be isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The term "hypervariable region" when used herein refers to the amino acid residues of an antibody that are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain. "Framework" or "FR" residues are those variable domain residues other than the hypervariable region residues as herein defined.

As used herein, the term "immunoadhesin" designates antibody-like molecules that combine the "binding domain" of a heterologous "adhesin" protein (e.g., a receptor, ligand or enzyme) with an immunoglobulin constant domain. Structurally, the immunoadhesins comprise a fusion of the adhesin amino acid sequence with the desired binding specificity that is other than the antigen recognition and binding site (antigen combining site) of an antibody (i.e., is "heterologous") and an immunoglobulin constant domain sequence.

An "antibody-immunoadhesin chimera" comprises a molecule that combines at least one binding domain of an antibody (as herein defined) with at least one immunoadhesin (as defined in this application).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptides will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide variant. This includes chronic and acute disorders or diseases including those pathological conditions that predispose the mammal to the disorder in question. In one embodiment, the disorder is a viral infection.

The word "label" when used herein refers to a detectable compound or composition that is conjugated directly or indirectly to the polypeptide. The label may itself be detectable (e.g., radioisotope labels or fluorescent labels) or, in the case of an enzymatic label, may catalyze chemical alteration of a substrate compound or composition that is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "molecular complex" when used herein refers to the relatively stable structure that forms when two or more heterologous molecules (e.g., polypeptides) bind (preferably noncovalently) to one another. The preferred molecular complex herein is an immune complex.

"Immune complex" refers to the relatively stable structure that forms when at least one target molecule and at least one heterologous Fc region-containing polypeptide bind to one another forming a larger molecular weight complex. Examples of immune complexes are antigen-antibody aggregates and target molecule-immunoadhesin aggregates. The term "immune complex" as used herein, unless indicated otherwise, refers to an ex vivo complex (i.e., other than the form or setting in which it may be found in nature). However, the immune complex may be administered to a mammal, e.g., to evaluate clearance of the immune complex in the mammal.

The term "target molecule" refers to a molecule, usually a polypeptide, which is capable of being bound by a heterologous molecule and has one or more binding sites for the heterologous molecule. The term "binding site" refers to a region of a molecule to which another molecule can bind. The "first target molecule" herein comprises at least two distinct binding sites (for example, two to five separate binding sites) for an analyte (e.g., an Fc region-containing polypeptide) such that at least two analyte molecules can bind to the first target molecule.

An "analyte" is a substance that is to be analyzed. The preferred analyte is an Fc region-containing polypeptide that is to be analyzed for its ability to bind to an Fc receptor.

A "receptor" is a polypeptide capable of binding at least one ligand.

The phrase "low affinity receptor" denotes a receptor that has a weak binding affinity for a ligand of interest, e.g., having a binding constant of about 50 nM or worse affinity. Exemplary low affinity receptors include FcγRII and FcγRIII.

In the following section, an approach to make some of the embodied compositions is provided.

Construction of Fc Deletion Mutants with Reduced Fcγ Receptor-Binding Affinity Activity A sequence alignment of IgG subtypes 1-4, including the sequences surrounding the deletions disclosed herein, is shown in FIG. 1.

The deletion mutants disclosed herein have a deletion of about nine amino acids (from about position 231 to about position 239) at the N-terminus of the $C_H2$ domain in the Fc region. By a deletion of "about nine" amino acids is meant a deletion of at least 4 amino acids having the sequence LLGG (Seq. Id. No. 1) and no more than about 10 amino acids. Chappel et al. (Chappel 1991 *Proc Natl Acad Sci USA* 88:9036-9040) identified the Fcγ receptor class I binding site in human IgG as the sequence spanning residues 234-237 (LLGG). For example, such deletions (Table 1) remove the following amino acids:

TABLE 1

Deleted Sequences

| Number of Amino Acids Deleted | Deleted Sequence | SEQ ID NO: |
|---|---|---|
| 4 | LLGG | 1 |
| 5 | ELLGG | 2 |
|  | LLGGP | 3 |
| 6 | PELLGG | 4 |
|  | ELLGGP | 5 |
|  | LLGGPS | 6 |
| 7 | APELLGG | 7 |
|  | PELLGGP | 8 |
|  | ELLGGPS | 9 |
|  | LLGGPSV | 10 |
| 8 | PAPELLGG | 11 |
|  | APELLGGP | 12 |
|  | PELLGGPS | 13 |
|  | ELLGGPSV | 14 |
| 9 | PAPELLGGP | 15 |
|  | APELLGGPS | 16 |
|  | PELLGGPSV | 17 |
| 10 | PAPELLGGPS | 18 |
|  | APELLGGPSV | 19 |

Embodiments herein relate to a method for making a polypeptide variant. The "parent", "starting" or "nonvariant" polypeptide is prepared using techniques available in the art for generating polypeptides comprising an Fc region. In some embodiments, the parent polypeptide is an antibody and exemplary methods for generating antibodies are described in more detail in the following sections. The parent polypeptide may, however, be any other polypeptide comprising an Fc region, e.g., an immunoadhesin. Methods for making immunoadhesins are elaborated in more detail hereinbelow.

In an alternative embodiment, a variant Fc region may be generated according to the methods herein disclosed and this "variant Fc region" can be fused to a heterologous polypeptide of choice, such as an antibody variable domain or binding domain of a receptor or ligand.

The parent polypeptide comprises an Fc region. Generally the Fc region of the parent polypeptide will comprise a native sequence Fc region, and preferably a human native sequence Fc region. However, the Fc region of the parent polypeptide may have one or more pre-existing amino acid sequence alterations or modifications from a native sequence Fc region. In a further embodiment the parent polypeptide Fc region is "conceptual" and, while it does not physically exist, the antibody engineer may decide upon a desired variant Fc region amino acid sequence and generate a polypeptide comprising that sequence or a DNA encoding the desired variant Fc region amino acid sequence. In some embodiments, however, a nucleic acid encoding an Fc region of a parent polypeptide is available and this nucleic acid sequence is altered to generate a variant nucleic acid sequence encoding the Fc region variant.

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Site-directed mutagenesis is a preferred method for preparing substitution variants. This technique is well known in the art (see, e.g., Kunkel et al. 1987 *Proc Natl Acad Sci USA* 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide. See *PCR Protocols: A guide to methods and applications*, Michael A. Innis, chapter by Higuchi, pp. 177-183 (Academic Press, 1990). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al. 1985 *Gene* 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Alternatively, or additionally, the desired amino acid sequence encoding a polypeptide variant can be determined, and a nucleic acid sequence encoding such amino acid sequence variant can be generated synthetically.

The amino acid sequence of the parent polypeptide is modified in order to generate a variant Fc region with altered Fc receptor binding affinity or activity in vitro and/or in vivo. One may, for example, delete about nine amino acids (from about position 231 to about position 239) at the N-terminus of the $C_H2$ domain in the Fc region. The Fc region herein comprising one or more amino acid deletions will preferably retain at least about 80%, and preferably at least about 90%, and most preferably at least about 95%, of the parent Fc region or of a native sequence human Fc region. Preferably, the parent polypeptide Fc region is a human Fc region, e.g., a native sequence human Fc region human IgG1 (A and non-A allotypes), IgG2, IgG3 or IgG4 Fc region.

The polypeptide variant(s) prepared as described above may be subjected to further modifications, oftentimes depending on the intended use of the polypeptide. Such modifications may involve further alteration of the amino acid sequence (substitution, insertion and/or deletion of amino acid residues), fusion to heterologous polypeptide(s) and/or covalent modifications. Such "further modifications" may be made prior to, simultaneously with, or following, the amino acid modification(s) disclosed above that result in an alteration of Fc receptor binding. In one embodiment, one may combine the Fc region modification herein with another Fc region modification. Alternatively or additionally, it may be useful to combine the above amino acid modifications with one or more further amino acid modifications that alter FcRn binding and/or half-life of the antibody.

With respect to further amino acid sequence alterations, any cysteine residue not involved in maintaining the proper conformation of the polypeptide variant also may be substituted, generally with serine, to improve the oxidative stability of the molecule and prevent aberrant cross linking. The polypeptide variant may be subjected to one or more assays to evaluate any change in biological activity compared to the starting polypeptide. Preferably the polypeptide variant essentially retains the ability to bind antigen compared to the nonvariant polypeptide, i.e., the binding capability is no worse than about 20 fold, e.g., no worse than about 5 fold of that of the nonvariant polypeptide. The binding capability of the polypeptide variant may be determined using techniques such as fluorescence activated cell sorting (FACS) analysis or radioimmunoprecipitation (RIA), for example. The ability of the polypeptide variant to bind an FcR may be evaluated. Where the FcR is a high affinity Fc receptor, such as FcγRI, FcRn or FcγRIIIA-V158, binding can be measured by titrating monomeric polypeptide variant and measuring bound polypeptide variant using an antibody that specifically binds to the polypeptide variant in a standard ELISA format. The following section provides more detail on approaches to produce antibodies.

Production of Antibodies

A description follows as to exemplary techniques for the production of the antibodies used in accordance with embodiments disclosed herein.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively)

with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler and Milstein 1975 *Nature* 256:495, or may be made by recombinant DNA methods.

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59 103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are SP-2 or X63-Ag8-653 cells available from the American Type Culture Collection, Manassas Va. USA. Human myeloma and mouse-human heteromyeloma cell lines also have been described for the production of human monoclonal antibodies (Brodeur et al., Monoclonal Antibody Production Techniques and Applications, pp. 51 63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells.

In a further embodiment, monoclonal antibodies or antibody fragments can be isolated from antibody phage libraries generated using the techniques described in the scientific literature. Researchers describe the isolation of murine and human antibodies using phage libraries. Some publications describe the production of high affinity (nM range) human antibodies by chain shuffling as well as combinatorial infection and in vivo recombination as a strategy for constructing very large phage libraries. Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences, or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522 525 (1986)), by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody. Another method uses a particular framework region derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The present application also contemplates affinity matured antibodies, which antibodies bind antigen. The parent antibody may be a human antibody or a humanized antibody. The affinity matured antibody preferably binds to antigen with an affinity superior to that of the parent antibody.

Various forms of the humanized or affinity matured antibody are contemplated. For example, the humanized or affinity matured antibody may be an antibody fragment. Alternatively, the humanized or affinity matured antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. Investigators isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated.

As discussed above, human antibodies may also be generated by in vitro activated B cells.

(v) Antibody Fragments

Various techniques have been developed for the production of antibody fragments. Traditionally, these fragments were derived via proteolytic digestion of intact antibodies. However, these fragments can now be produced directly by recombinant host cells. For example, the antibody fragments can be isolated from the antibody phage libraries discussed above.

(vi) Bispecific Antibodies

Bispecific antibodies are antibodies that have binding specificities for at least two different epitopes. Methods for making bispecific antibodies are known in the art. Traditional production of full length bispecific antibodies is based on the coexpression of two immunoglobulin heavy chain-light chain pairs, where the two chains have different specificities. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

According to another approach, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells. Heteroconjugate antibodies may be made using any convenient cross-linking methods. Suitable cross-linking agents are well known in the art, along with a number of cross-linking techniques.

Antibodies with more than two valencies are contemplated. For example, trispecific antibodies can be prepared.

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis". Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

Amino Acid Substitutions

| Original Residue | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
 (1) hydrophobic: norleucine, met, ala, val, leu, ile;
 (2) neutral hydrophilic: cys, ser, thr;
 (3) acidic: asp, glu;
 (4) basic: asn, gln, his, lys, arg;
 (5) residues that influence chain orientation: gly, pro; and
 (6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of an embodiment with respect to effector function. Alternatively or additionally, cysteine residue(s) may be introduced in the Fc region, thereby allowing interchain disulfide bond formation in this region. Homodimeric antibodies with enhanced anti-tumor activity may be prepared using heterobifunctional cross-linkers. Alternatively, an antibody can be engineered that has dual Fc regions.

To increase the serum half-life of the antibody, one may incorporate a salvage receptor binding epitope into the antibody. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. The next section describes approaches to design and generate immunoadhesins.

Immunoadhesin Preparation

The simplest and most straightforward immunoadhesin design combines the binding domain(s) of the adhesin (e.g., the extracellular domain (ECD) of a receptor) with the Fc region of an immunoglobulin heavy chain. Ordinarily, when preparing the immunoadhesins, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain. The precise site at which the fusion is made is not critical; particular sites are well known and may be selected in order to optimize the biological activity, secretion, or binding characteristics of the immunoadhesin.

In one embodiment, the adhesin sequence is fused to the N-terminus of the Fc region of immunoglobulin G1 (IgG1). It is possible to fuse the entire heavy chain constant region to the adhesin sequence. However, more preferably, a sequence beginning in the hinge region just upstream of the papain cleavage site that defines IgG Fc chemically (i.e., residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimers, each of the four units may be the same or different.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains.

Although the presence of an immunoglobulin light chain is not required in the immunoadhesins of embodiments disclosed herein, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs.

Immunoadhesins are most conveniently constructed by fusing the cDNA sequence encoding the adhesin portion in-frame to an immunoglobulin cDNA sequence. However, fusion to genomic immunoglobulin fragments can also be used. The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells. The next section describes various approaches, including in vitro assays and in vivo assays, to screen for suitable antibodies.

Screening for Antibodies with the Desired Properties

Binding affinity can be measured in a variety of ways. Generally, and regardless of the precise manner in which affinity is defined or measured, the methods of embodiments disclosed herein reduce binding affinity to FcR. The methods generate a polypeptide that is superior to the starting polypeptide from which it was made (for example, the methods of embodiments disclosed herein are considered effective or successful when a modified polypeptide, e.g., has a better clinical outcome than the starting polypeptide).

Reduction in Fc receptor binding of a polypeptide can be determined by measuring its binding affinity for a particular Fc receptor. In one embodiment, this can be determined by measuring the binding affinity of the altered polypeptide for an Fc gamma receptor.

Reduction in the binding affinity of an altered polypeptide may be determined by comparing the binding affinity of the altered polypeptide with a suitable control polypeptide (e.g., the corresponding starting polypeptide). In one embodiment, reduction of binding affinity may be determined by comparing the binding affinity of the altered polypeptide in a first assay with the binding affinity of the control polypeptide in a second binding assay. In alternative embodiments, reduction of binding affinity may be determined by comparing the binding affinity of the altered polypeptide and the control polypeptide in the same assay. For example, the assay may be performed as a competitive binding assay where the binding affinity of the altered polypeptide is evaluated with increasing concentrations of the control polypeptide.

(i) Cell-Free Assays

Several in vitro, cell-free assays for testing the effector functions (e.g., FcR binding affinity) of altered polypeptides have been described in the art. Preferably, the cell-free assay is capable of evaluating binding of altered antibodies to soluble forms of Fc receptors. Automation and high throughput screening (HTS) technologies may be utilized in the screening procedures. Screening may employ the use of labels (e.g., isotopic labels, chromophores, fluorophores, lumiphores, or epitopes) that enable detection. The labels may be attached to the Fc receptor or the Fc-containing polypeptide that is assayed.

Exemplary cell-free assays include, but are not limited to, FRET (fluorescence resonance energy transfer), BRET (bioluminescence resonance energy transfer), Alphascreen (Amplified Luminescent Proximity Homogeneous)-based assays, scintillation proximity assays, ELISA (enzyme-linked immunosorbent assays), SPR (surface plasmon resonance, such as BIACORE), isothermal titration calorimetry, differential scanning calorimetry, gel electrophoresis, analytical ultracentrifugation, and chromatography, including gel-filtration chromatography.

(ii) Cell-Based Assays

Several in vitro, cell-based assays for testing the effector functions (e.g., FcR binding affinity) of altered polypeptides have been described in the art. Preferably, the cell-based assay is capable of evaluating binding of altered antibodies to surface forms of the Fc receptors. Exemplary cell-based assays include bridging assays and flow cytometry.

In an exemplary embodiment, the FcR binding affinity of an altered antibody can be measured using an FcR bridging assay. FcR (e.g., FcN or FcγR) binding affinities can be measured with assays based on the ability of the antibody to form a "bridge" between antigen and an FcR bearing cell.

(iii) Model Animal Assays

The altered polypeptides of embodiments disclosed herein may also be administered to a model animal to test its potential for use in prophylaxis or therapy, either for veterinary purposes or as an animal model of human disease, e.g., by testing the effector function of the antibody. Regarding the latter, such animal models may be useful for evaluating the prophylactic or therapeutic efficacy of antibodies of embodiments disclosed herein (e.g., testing of effector function, dosages, and time courses of administration). The next section describes pharmaceutical formulations of the antibodies that can be used in accordance with embodiments disclosed herein.

Pharmaceutical Formulations

Prophylactic or therapeutic formulations of the antibodies used in accordance with embodiments disclosed herein are prepared for storage by mixing an antibody having the desired degree of purity with optional pharmaceutically acceptable carriers, excipients or stabilizers (*Remington's Pharmaceutical Sciences,* $18^{th}$ ed., 1990, Mack Publishing Co., Easton, Pa.), in the form of lyophilized formulations or aqueous solutions. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorchinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being prevented or treated, preferably those with complementary activities that do not adversely affect each other. For example, it may be desirable to further provide antibodies that bind to other targets (e.g., an antibody that binds a different epitope). Alternatively, or additionally, the composition may further comprise antiviral agent(s). Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 18$^{th}$ ed., 1990, Mack Publishing Co., Easton, Pa.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. The formulations to be used for in vivo administration must be sterile. This is readily accomplished by filtration through sterile filtration membranes. The following section describes alternative, non-therapeutic uses for the polypeptide variants of embodiments disclosed herein.

Non-Therapeutic Uses for the Polypeptide Variant

The polypeptide variant may be useful in diagnostic assays, e.g., for detecting expression of an antigen of interest in specific cells, tissues, or serum. For diagnostic applications, the polypeptide variant typically will be labeled with a detectable moiety. Radioisotopes, such as $^{35}$S, $^{14}$C, $^{125}$I, $^{3}$H, and $^{131}$I are available. The polypeptide variant can be labeled with the radioisotope using the techniques described in *Current Protocols in Immunology*, Volumes 1 and 2, Coligen et al., Ed. Wiley-Interscience, New York, N.Y., 1991, for example, and radioactivity can be measured using scintillation counting. Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in *Current Protocols in Immunology*, supra, for example. Fluorescence can be quantified using a fluorimeter. In addition, various enzyme-substrate labels are available. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase, luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Sometimes, the label is indirectly conjugated with the polypeptide variant. The skilled artisan will be aware of various techniques for achieving this. For example, the polypeptide variant can be conjugated with biotin and any of the three broad categories of labels mentioned above can be conjugated with avidin, or vice versa. Biotin binds selectively to avidin and thus, the label can be conjugated with the polypeptide variant in this indirect manner. Alternatively, to achieve indirect conjugation of the label with the polypeptide variant, the polypeptide variant is conjugated with a small hapten (e.g., digoxigenin) and one of the different types of labels mentioned above is conjugated with an anti-hapten polypeptide variant (e.g., anti-digoxigenin antibody). Thus, indirect conjugation of the label with the polypeptide variant can be achieved. In another embodiment, the polypeptide variant need not be labeled, and the presence thereof can be detected using a labeled antibody that binds to the polypeptide variant.

The polypeptide variant of embodiments disclosed herein may be employed in any known assay method, such as competitive binding assays, direct and indirect sandwich assays, and immunoprecipitation assays. The polypeptide variant may also be used for in vivo diagnostic assays. Generally, the polypeptide variant is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

If a mutation in a flavivirus sequence proves to be a major determinant of an ADE epitope (e.g., a DEN-4 variant), such variant can be explored to address vaccine safety related to ADE. This embodiment is directed to methods for selecting a determinant of an ADE epitope. This method comprises screening for determinants that generate antibodies, which are sub-neutralizing or non-neutralizing, as compared to neutralizing, to identify at least one ADE epitope. The next section describes in vivo applications for the polypeptide variants of embodiments disclosed herein.

In Vivo Uses for the Polypeptide Variant

It is contemplated that the polypeptide variant of embodiments disclosed herein may be used for the prophylaxis or treatment of a mammal e.g., a patient suffering from, or predisposed to, a disease or disorder who could benefit from administration of the polypeptide variant.

The polypeptide variant is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the polypeptide variant is suitably administered by pulse infusion, particularly with declining doses of the polypeptide variant. Preferably the dosing is given by injections, most preferably intravenous or subcutaneous injections, depending in part on whether the administration is brief or chronic.

For the prevention or treatment of disease, the appropriate dosage of polypeptide variant will depend on the type of disease to be prevented or treated, the severity and course of the disease, whether the polypeptide variant is administered for preventive or therapeutic purposes, previous prophylaxis and therapy, the patient's clinical history and response to the polypeptide variant, and the discretion of the attending physician. The polypeptide variant is suitably administered to the patient at one time or over a series of treatments.

In one embodiment, the altered polypeptides of some embodiments are advantageously used for passive immunization against a disease complicated by antibody-dependent enhancement (ADE). Antibody-dependent enhancement, a phenomenon in which viral replication is increased rather than decreased by immune sera, has been observed for a large number of viruses of public health importance, including flaviviruses, coronaviruses, and retroviruses.

For passive immunization with an antibody, about 1 μg/kg to 15 mg/kg (e.g., 0.1 20 mg/kg) of polypeptide variant is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the prophylaxis or treatment is sustained until a desired suppression or modification of disease symptoms occurs. However, other dosage regimens may be useful. The progress of this therapy is easily monitored by conventional techniques and assays.

The polypeptide variant composition will be formulated, dosed, and administered in a fashion consistent with good medical practice. Factors for consideration in this context include the particular disorder being prevented or treated, the particular mammal being treated, the clinical condition of the individual patient, the cause of the disorder, the site of delivery of the agent, the method of administration, the scheduling of administration, and other factors known to medical practitioners. The "prophylactically or therapeutically effective amount" of the polypeptide variant to be administered will be governed by such considerations, and is the minimum amount necessary to prevent, ameliorate, or treat a disease or disorder. The polypeptide variant need not be, but is optionally formulated with one or more agents currently used to prevent or treat the disorder in question. The effective amount of such other agents depends on the amount of polypeptide variant present in the formulation, the type of disorder or treatment, and other factors discussed above. These are generally used in the same dosages and with administration routes as used hereinbefore or about from 1 to 99% of the heretofore employed dosages.

The following examples provide illustrations of some of the embodiments described herein but are not intended to limit invention.

EXAMPLE 1

Monoclonal Antibody-Mediated Enhancement of Dengue Virus Infection In Vitro and In Vivo and Strategies of Prevention Infection with dengue virus (DENV) or any other flavivirus induces cross-reactive, but weakly- or non-neutralizing antibodies that recognize epitopes involving the fusion peptide in the envelope glycoprotein (E). Humanized monoclonal antibody (MAb) IgG 1A5, derived from a chimpanzee, shares properties of cross-reactive antibodies. MAb IgG 1A5 up-regulated DENV infection by a mechanism of antibody-dependent enhancement (ADE) in a variety of Fc receptor-bearing cells in vitro. A 10- to 1000-fold increase of viral yield in K562 cells, dependent on the DENV serotype, was observed over a range of sub-neutralizing concentrations of IgG 1A5. A significant increase of DENV-4 viremia titers (up to 100 fold) was also demonstrated in juvenile rhesus monkeys immunized with passively transferred dilutions of IgG 1A5. These results, together with earlier findings of ADE of DENV-2 infection by a polyclonal serum, establish the primate model for analysis of ADE. Considering the abundance of these cross-reactive antibodies, our observations confirm that significant viral amplification could occur during DENV infections in humans with prior infection or with maternally transferred immunity, possibly leading to severe dengue. Strategies to eliminate ADE were explored by altering the antibody Fc structures responsible for binding to Fc receptors. IgG 1A5 variants, containing amino acid substitutions from the Fc region of IgG2 or IgG4 antibodies reduced, but did not eliminate DENV-4-enhancing activity in K562 cells. Importantly, a 9-amino-acid deletion at the N-terminus of the $C_H2$ domain in the Fc region abrogated the enhancing activity.

ADE of DENV Infection Mediated by IgG 1A5 in K562 Cells

Figure 2:
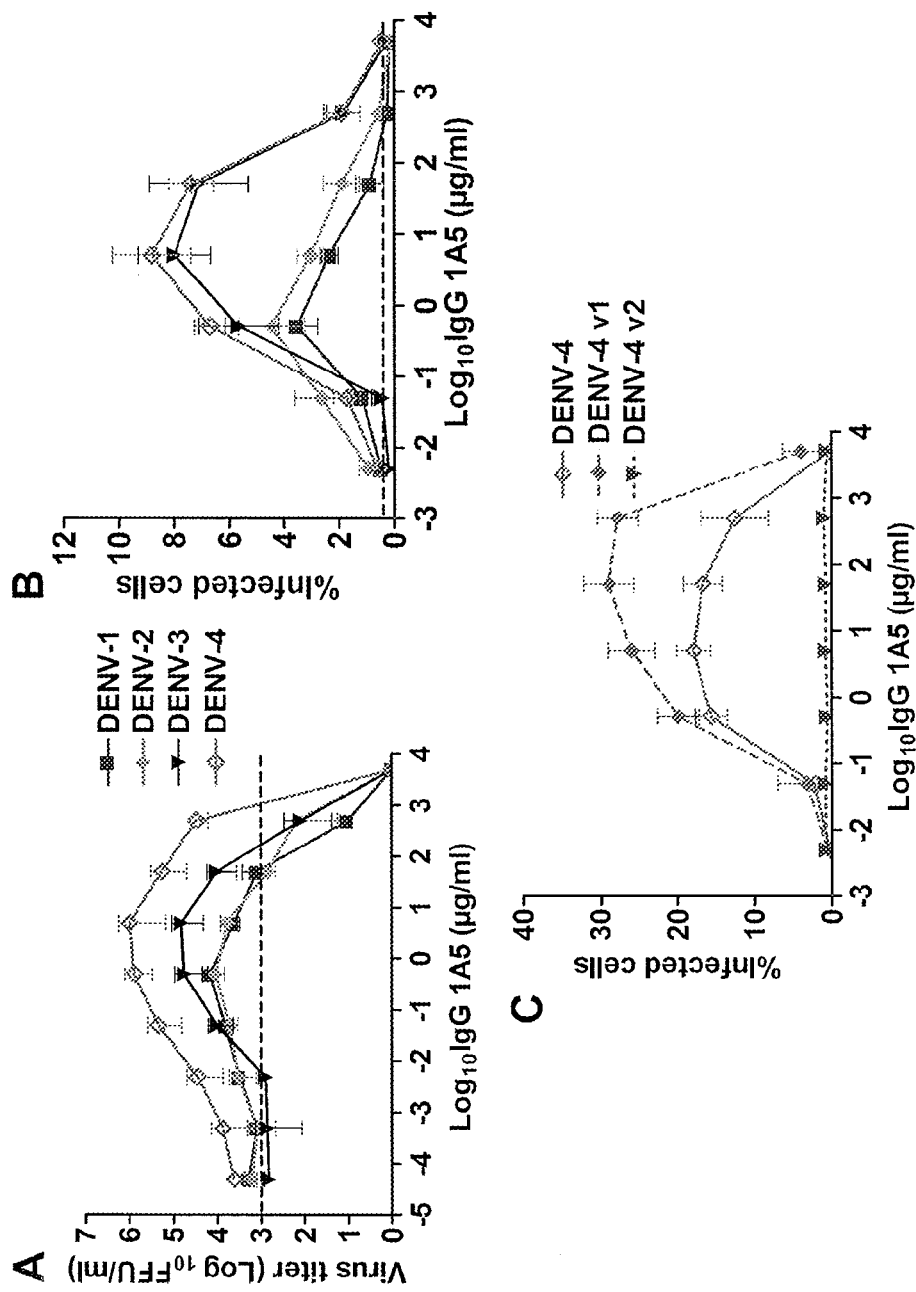
FIG. 2. ADE of DENV replication in K562 cells mediated by varying concentrations of IgG 1A5. (A) Increase of the viral yields (FFU/ml) of each DENV serotype. The baseline viral yield (dashed line) was approximately 1000 FFU/ml using a DENV sero-negative human IgG1 as control. (B) Percent of cells infected with DENV detected by flow cytometry. (C) Percent of cells infected with 1 MOI of DENV-4 or antigenic variant detected by flow cytometry. Variant DENV-4 v1 contains substitution $Leu_{107}Phe$ and variant DENV-4 v2 contains substitution $Gly_{106}Val$ in E.

The MOI of each DENV for K562 cells was adjusted to produce a viral yield of approximately 3 $\log_{10}$ FFU/ml 4 days after infection in the absence of added antibody. DENV-2 required an MOI of 0.05, whereas DENV-1 and DENV-4 required an MOI of 0.10 and DENV-3 an MOI of 0.15 for such an infection. The viral yield from DENV infection in the presence of a DENV-negative human IgG1 was the same as for the control. To analyze the ADE of DENV infection in K562 cells, each DENV was pre-incubated with dilutions of IgG 1A5 ($10^{-3}$ to $10^4$ µg/ml) to form immune complexes prior to infecting K562 cells. Neutralization of DENV infection at high IgG 1A5 concentrations and a break-through at lower concentrations occurred. Further dilutions of IgG 1A5 led to an increase of viral yields, consistent with the ADE phenomenon (FIG. 2A). The maximum viral yield above baseline was approximately 10 fold for DENV-1 and DENV-2, 54 fold for DENV-3 and 1000 fold for DENV-4. The antibody concentration that mediated the maximum increase was approximately 0.5 µg/ml for DENV-1 and DENV-2 and 5 µg/ml for DENV-3 and DENV-4, similar to the $PRNT_{50}$ titer against that DENV serotype (Goncalvez, A. P. et al. 2004 *J Virol* 78:12910-12918).

The IgG 1A5-dependent enhancement of DENV infection was also analyzed by flow cytometry. Each DENV produced approximately a 0.5% cell infection rate with DENV-negative human IgG1 2 days after incubation. In the presence of IgG 1A5, infected cells were increased up to 4.5% for DENV-1 and DENV-2 and up to 11.5% for DENV-3 and DENV-4 (FIG. 2B). The optimum antibody concentration for the enhancement of DENV infection was similar to that observed by focus assay.

The difference in ADE activities among the different DENV serotypes was probably due to sequence variations in the antibody-binding sites. This possibility was explored by ADE analysis using DENV-4 antigenic variants containing $Gly_{106}Val$ or $Leu_{107}Phe$ substitution in E, which reduced their antibody-binding affinity (Goncalvez, A. P. et al. 2004 *J Virol* 78:12919-12928). Infection of K562 cells with IgG 1A5-low-binding DENV-4 $Gly_{106}Val$ (DENV-4 v2) was not enhanced by the antibody. In contrast, IgG 1A5 enhanced infection of IgG 1A5-moderate-binding DENV-4 $Leu_{107}Phe$ (DENV-4 v1) variant in K562 cells to 28.9±3.2%, compared to parental DENV-4 (18.0±2.2%) (FIG. 2C). The optimum IgG 1A5 concentration for infection was 50 µg/ml, similar to the $PRNT_{50}$ titer of the variant.

Figure 3:
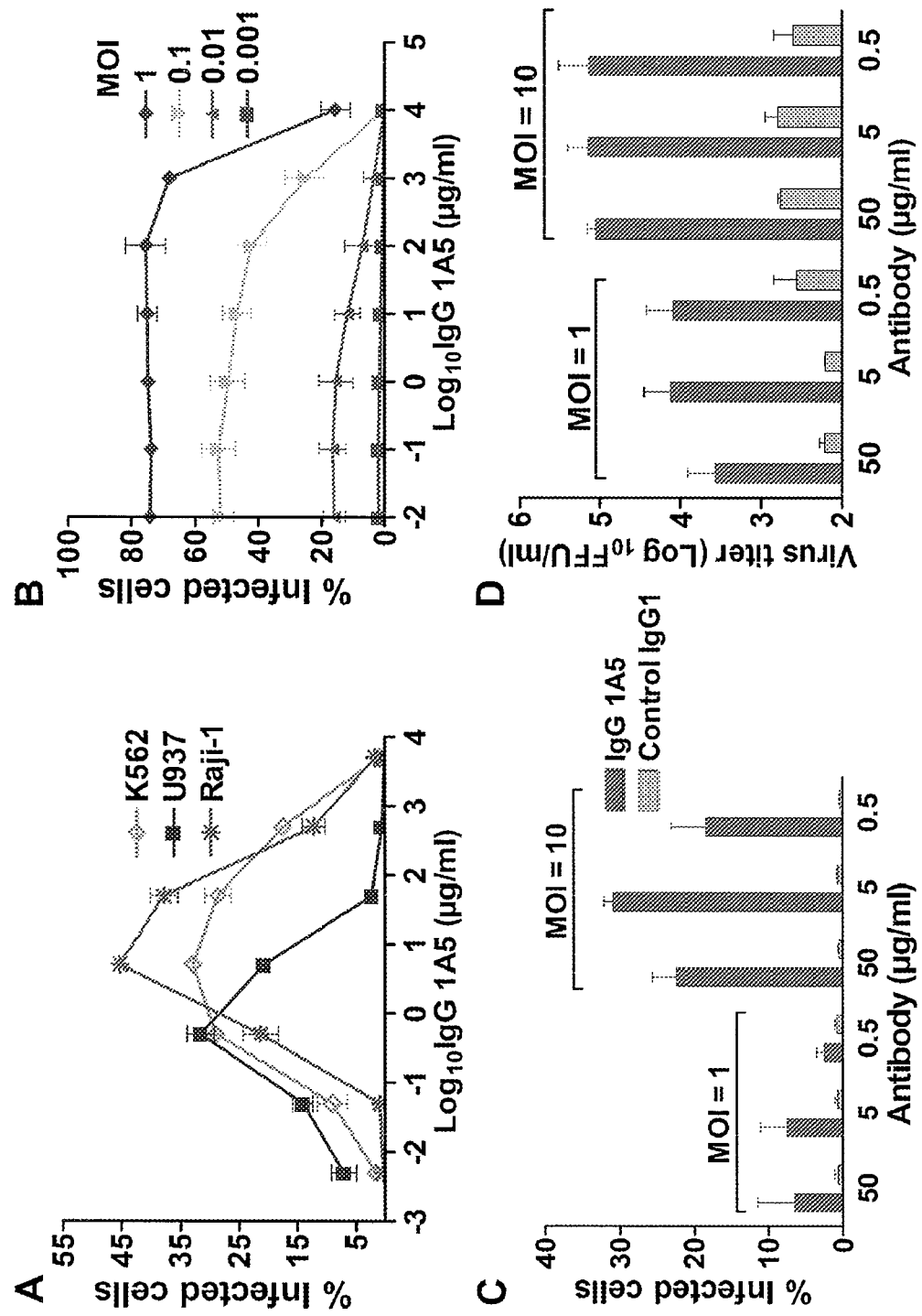
FIG. 3. ADE of DENV-4 infection in other Fc R-bearing cells mediated by IgG 1A5. (A) ADE in U937 and Raji-1 cells infected with 1 MOI, detected by flow cytometry. (B) ADE in DC-SIGN-expressing Raji-1 cells, detected by flow cytometry. (C) ADE in monkey primary monocytes, detected by flow cytometry. (D) Same as in (C) but detected by the viral yield.

IgG 1A5-Mediated Enhancement of DENV-4 Infection in Other Fc R-Bearing Cells and in Rhesus Monkey Primary Monocytes Whether other Fc R-bearing cells would also support IgG 1A5-mediated enhancement of DENV-4 replication was determined. At a MOI of 1 and in the absence of antibody, flow cytometry detected 5.3±2.7% infection in U937 cells and 0.35±0.03% in Raji-1 cells. A consistent increase of DENV-4 infection, up to 31.5±2.3% in U937 cells and 45.2±1.0% in Raji-1 cells, was detected when the virus was mixed with the antibody at varying concentrations (FIG. 3A). IgG 1A5 failed to mediate enhancement of DENV-4 infection in Raji-1 (DC-SIGN) cells expressing DC-SIGN, which has been shown to facilitate DENV infection by a mechanism different from ADE (Tassaneetrithep, B. et al. 2003 *J Exp Med* 197:823-829) (FIG. 3B).

IgG 1A5-mediated enhancement of DENV-4 infection in primary monocytes from juvenile rhesus monkeys was also analyzed. At a MOI of 1 or 10 and in the presence of dengue-negative human serum, <1% of the monocytes was infected with DENV-4. The number of infected cells detected by flow cytometry reached 31±1.2%, when IgG 1A5 was added at 5 µg/ml (FIG. 3C). A 1000-fold enhancement of DENV-4 replication was detected with 0.5, 5 and 50 µg/ml of IgG 1A5, when analyzed by focus assay (FIG. 3D).

Enhancement of DENV-4 Infection Mediated by IgG 1A5 in Juvenile Rhesus Monkeys

Figure 4:
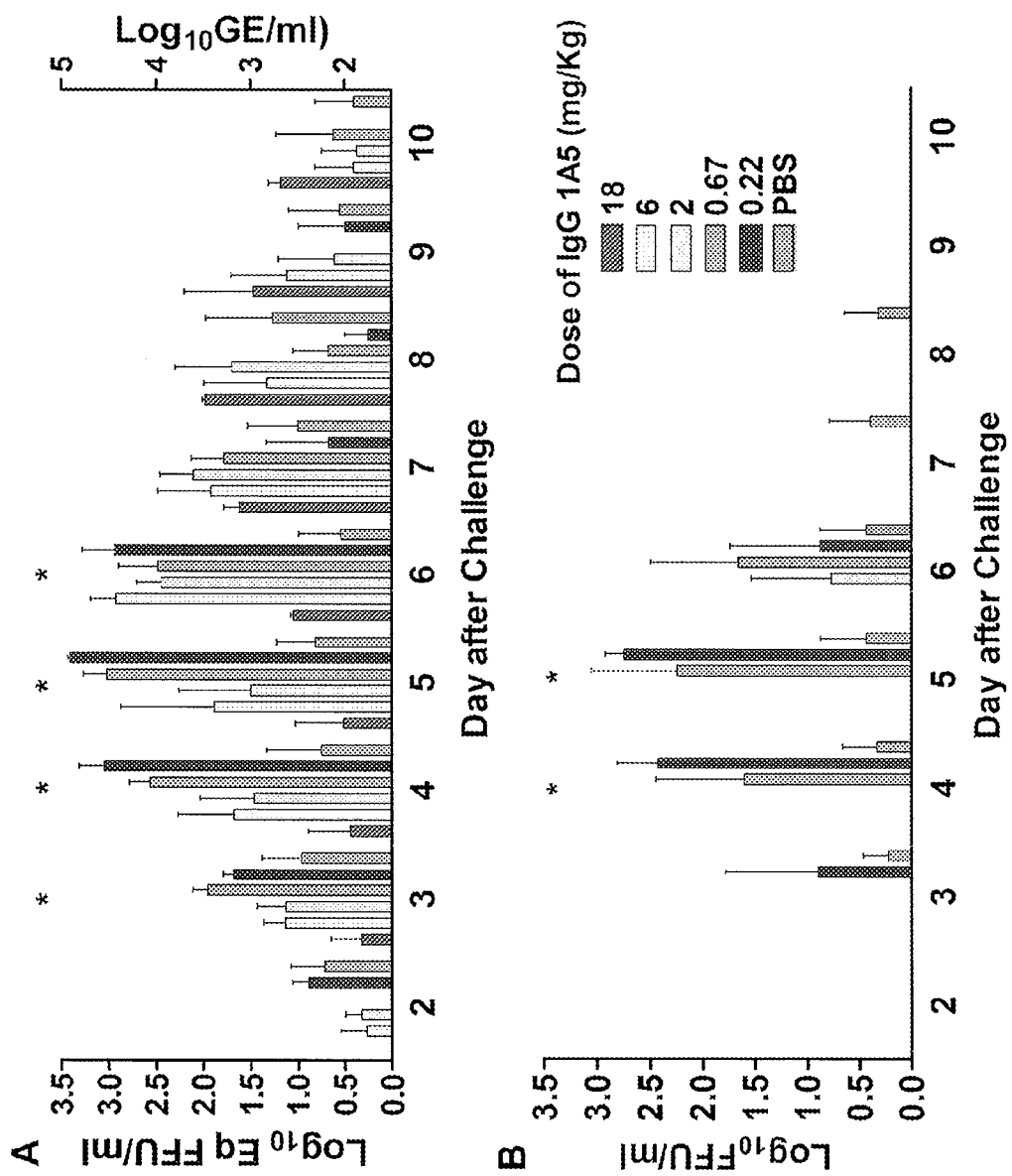
FIG. 4. ADE of DENV-4 infection in juvenile rhesus monkeys passively administered with IgG 1A5. (A) Viremia titer in monkeys, detected by qPCR. The results are expressed in genome equivalent (GE) and equivalent (Eq) FFU/ml. The viremia titers on days 3-6 (indicated by asterisks) for the monkey groups receiving 6, 2.0, 0.67, and 0.22 mg/kg IgG 1A5 were significantly different from that of the control group that received PBS. (B) Same as in (A), except that the viremia titer was determined by a direct FFU assay. The variation bars indicate the titer differences (standard error) among monkeys in each group.

The experiment included 18 monkeys in groups of three: five groups to receive IgG 1A5 antibody intravenously at various concentrations and the sixth group to receive PBS diluent as a control. The serum IgG 1A5 concentrations 24 h after infusion (prior to DENV-4 challenge) were confirmed by ELISA and by plaque reduction neutralization test (Table 3). FIG. 4A shows the result of average DENV-4 viremia titers from days 2-10 for each group of monkeys. The viremia titers on these days were not significantly different between the monkey group that received 18 mg/kg of IgG 1A5 and the monkey group that received PBS. By comparison, a significant difference in the viremia titer in all monkey groups was observed for days 3-6 after challenge ($P<0.05$; Kruskal-Wallis test). Based on the analysis of these four days, qPCR detected a mean peak viremia titer of 0.76 $\log_{10}$ FFU/ml in the control group. The mean viremia titer increased from 0.58 to 2.76 $\log_{10}$ FFU/ml in the groups, as antibody concentration decreased from 18 to 0.22 mg/kg (Table 4). The viremia titer increased ~15 and ~8 fold in the monkey groups that received 6 and 2 mg/kg IgG 1A5, respectively, compared to that observed in the control group ($P<0.05$; Mann-Whitney U test). The monkey groups administered 0.67 and 0.22 mg/kg IgG 1A5 had nearly ~56 and ~100 fold increases in viral titers, respectively, a highly significant increase compared with that observed in the control group ($P<0.001$; Mann-Whitney U test).

TABLE 3

Serum concentration and neutralizing activity of different doses of IgG 1A5, 24 h after infusion into groups of monkeys

| IgG 1A5 dose, mg/kg | IgG 1A5 concentration (µg/ml)[b] ± SD | | Serum PRNT$_{50}$ titer (1/dilution)[c] ± SD |
|---|---|---|---|
| | Predicted[a] | Measured[b] | |
| 18 | 180 | 166.3 ± 25.5 | 38.5 ± 3.9 |
| 6 | 60 | 56.3 ± 4.5 | 11.8 ± 2.9 |
| 2 | 20 | 22.7 ± 0.6 | 5.6 ± 0.6 |
| 0.67 | 6.7 | 7.2 ± 0.3 | <5 |
| 0.22 | 2.2 | 3.1 ± 0.6 | <5 |
| Control (PBS) | 0 | <2 × 10$^{-3}$ | <5 |

[a] Serum IgG 1A5 concentration was calculated on the basis of 5% weight blood volume and dose given to each monkey.
[b] Mean serum IgG 1A5 concentration on the day of challenge, determined by ELISA.
[c] Serum PRNT$_{50}$ titer was the reciprocal of dilution that gave 50% plaque reduction on Vero cells.

TABLE 4

Peak viremia titers in serum of monkeys passively transferred with IgG 1A5 then infected with DENV-4

| Monkey group Dose of IgG | Geometric mean peak viremia titer ($\log_{10}$FFU/ml ± SE) determined by | |
|---|---|---|
| 1A5 (mg/kg) | qPCR[a] | Focus assay[b] |
| 18 | 0.58 ± 0.16 | ≤0.60 |
| 6 | 1.92 ± 0.37[c] | ≤0.60 |
| 2 | 1.64 ± 0.28[c] | ≤0.60 |
| 0.67 | 2.51 ± 0.22[d] | 1.92 ± 0.31[c] |
| 0.22 | 2.76 ± 0.38[d] | 2.58 ± 0.16[c] |
| Control (PBS) | 0.76 ± 0.10 | 0.40 ± 0.05 |

[a] Mean peak viremia titer was based on days 3 to 6 after infection ($P<0.05$; Kruskal-Wallis test).
[b] Mean peak viremia titer was calculated on days 4 and 5 after infection ($P<0.05$).
[c] $P<0.05$ and
[d] $P<0.001$ (Mann-Whitney U test).

The viremia titers of infected monkeys were also determined by FFU assay. Viremia was detected on days 3 to 8 after challenge in the control group, but not in the monkey groups that received 18 and 6 mg/kg of IgG 1A5 (FIG. 4B). Compared to the mean viremia titer in the control group (0.40 $\log_{10}$ FFU/ml), a significant difference in the viremia titer was observed across the monkey groups that received lower IgG 1A5 concentrations on days 4 and 5 ($P<0.05$; Kruskal-Wallis test). The mean viremia titer in the monkey groups that received 0.67 and 0.22 mg/kg of antibody increased ~36 and ~165 fold, respectively ($P<0.05$; Mann-Whitney U test) (Table 4).

The time of peak viremia was delayed 2-3 days in the monkey group that received the highest dose of IgG 1A5, compared to the monkey groups that received lower doses of antibody or PBS. The high antibody concentration might have reduced DENV-4 replication and selected for escape variants in these monkeys. The latter possibility was ruled out by sequencing the E-specific DNA amplified from viremic samples on days 7, 8 and 9 after challenge, as no mutation was found in the sequence. DENV-4 infection in monkeys was also confirmed by sero-analysis six weeks after challenge. Semi-quantitative analysis by radio-immunoprecipitation revealed that the levels of anti-NS1 antibody, an indirect measure of the extent of DENV replication, were significantly higher in the monkey groups that received antibody, except for the group that received 18 mg/kg, compared to that of the control group (P=0.049). Thus, analysis of anti-NS1 antibodies also supported IgG 1A5-mediated enhancement of DENV-4 replication in the primates.

Figure 5:
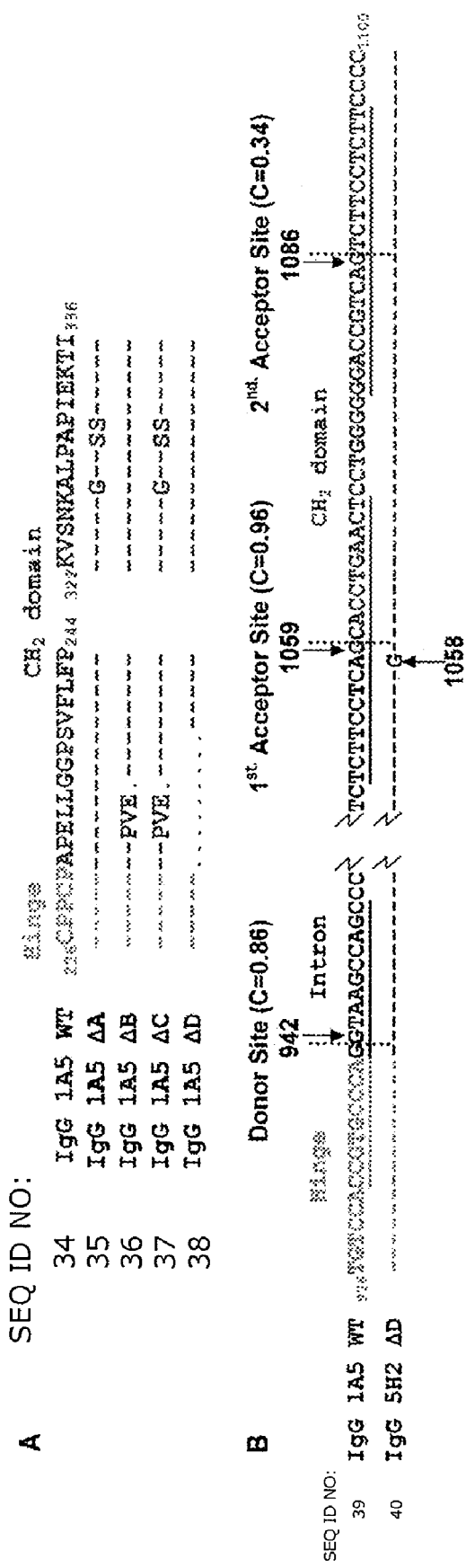
FIG. 5. (A) IgG 1A5 variants containing sequence alterations in the Fc that affect Fc receptor binding. The regions at positions 233-236 and at positions 327-331 are known to contribute to Fc R binding. The N-terminus of $C_H2$ is located at position 231 according to the numbering system used. The substitution sequences in ΔA, ΔB and ΔC and the deletion sequence (represented by dots in ΔD) of the IgG 1A5 constructs are shown. (B) Altered splicing of mRNA to generate a 9-amino-acid deletion in the Fc of IgG 5H2 ΔD. The illustration depicts a probable mechanism by which substitution of $A_{1058}G$ in IgG 5H2 AD renders the normal acceptor splice site at 1059 defective. Alternate splicing occurs at nucleotide position 1086 to generate the 9-amino-acid deletion. C is the confidence value based on the sequence (underlined) for splicing to take place according to the NetGene 2 program (Brunak, S. et al. 1991 *J Mol Biol* 220:49-65).
Figure 6:
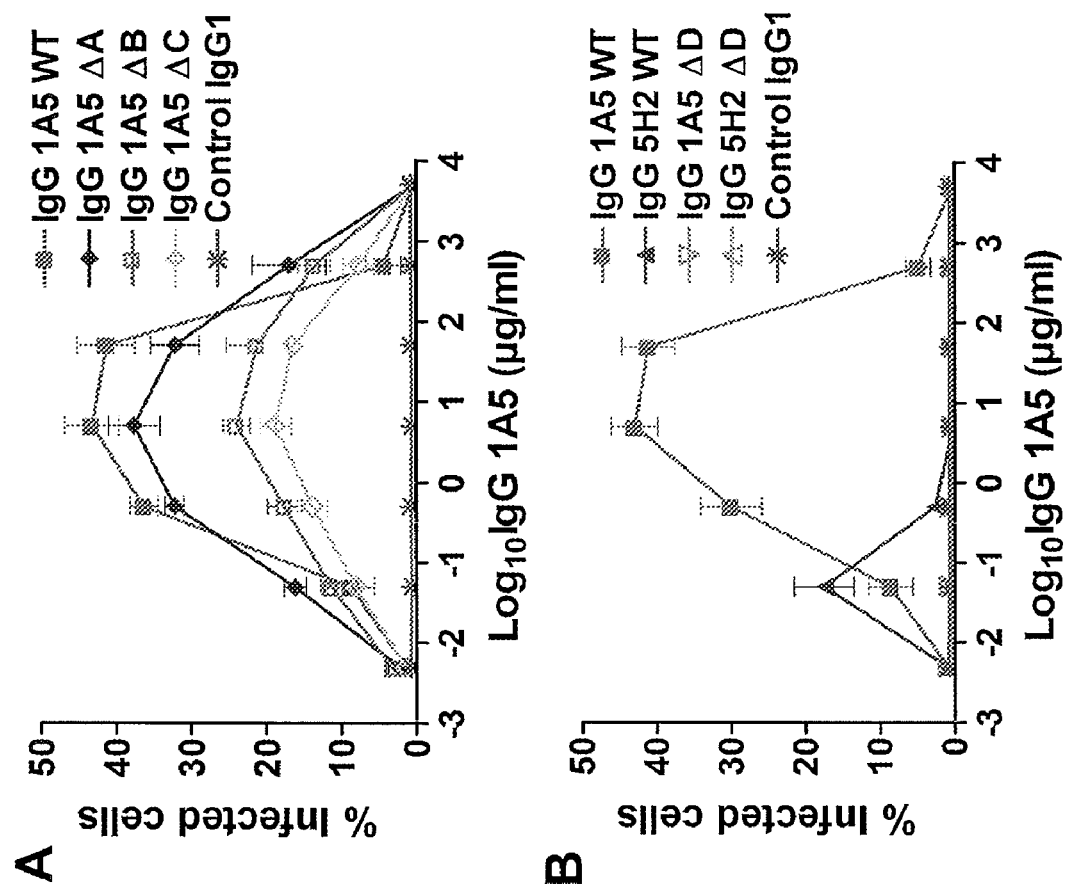
FIG. 6. ADE of DENV-4 infection at 1 MOI in K562 cells mediated by IgG 1A5 Fc variants. (A) IgG 1A5 variants containing sequence substitutions of subclass IgG2 or IgG4 in the Fc. (B) ADE activity of IgG 1A5 abrogated by the 9-amino-acid deletion (ΔD) in the Fc region originally identified in IgG 5H2 ΔD. Dengue-negative human serum was used as control.

Mutations in the Fc Region of IgG 1A5 Reduced or Eliminated ADE of DENV-4 Infection Sequences in the Fc region of IgG 1A5 were replaced with the analogous sequences of IgG2 or IgG4 subclass, which have reduced Fcγ receptor-binding affinity (Armour, K. L. et al. 1999 *Eur J Immunol* 29:2613-2624). Three variants were constructed: (1) IgG 1A5 ΔA contained replacement amino acids at 327, 330 and 331 in the Fc of IgG4; (2) IgG 1A5 ΔB contained replacement amino acids at 233-236 in the Fc of IgG2; (3) IgG 1A5 ΔC contained replacements of both variants ΔA and ΔB (FIG. 5A). Enhancement of DENV-4 infection in K562 cells mediated by each of these antibody variants was analyzed by flow cytometry. Compared to the enhancing activity of parental IgG 1A5 (43.3±3.6% of cells infected), the enhancing activity of variant IgG 1A5 ΔA was 37.6±3.5%, variant IgG 1A5 ΔB was 24.0±1.8% and variant IgG 1A5 ΔC was 18.8±2.1% of cells infected. Thus, these Fc variants of IgG 1A5 diminished the DENV-4 enhancing activity of IgG 1A5 by up to 2.3 fold, but did not eliminate it (FIG. 6A).

The enhancing activity of DENV cross-reactive IgG 1A5 was compared with that of DENV-4-specific IgG 5H2. IgG 5H2 had no detectable enhancing activity of DENV-4 infection in K562 cells and other monocyte lines. IgG 5H2 also did not appear to enhance DENV-4 replication in transfected CV-1 cells expressing FcγRI (CD64+). These observations prompted us to sequence mRNA from transformed CHO cells expressing IgG 5H2. Surprisingly, the coding sequence showed a deletion of 9 amino acids (positions 231-239) at the N-terminus of the $C_H2$ domain in the Fc region. Sequence analysis of the plasmid construct also revealed an $A_{1058}G$ substitution within the intron preceding the acceptor splice site (FIG. 4B). The substitution was not present in the original plasmid vector, nor in other IgG expression plasmids derived from it. The fortuitously introduced mutation rendered the splice site defective and, instead, an alternative splice site was used to generate new mRNA of IgG 5H2 heavy chain with the 9-amino-acid deletion (designated ΔD), as predicted according to the NetGene2 program (Brunak, S. et al. 1991 *J Mol Biol* 220:49-65).

To explore the mechanism of altered mRNA splicing, the $A_{1058}G$ mutation was introduced into the IgG 1A5-expressing plasmid. Analysis of mRNA from transfected cells confirmed the predicted 9-amino-acid deletion in IgG 1A5 ΔD (FIG. 4A). The level of IgG 1A5 ΔD expression was low, compared to that of IgG 1A5. To increase antibody production, another variant of IgG 1A5 ΔD was constructed by deleting the entire 27 nucleotides coding for amino acids 231-239 in the $C_H2$ domain, maintaining the normal splice junction (FIG. 5B). IgG 1A5 ΔD did not mediate detectable enhancement of DENV-4 infection in K562 cells (FIG. 6B). Conversely, full-length IgG 5H2 was produced by restoring the wild type sequence in the expression plasmid and the product was shown to mediate enhancement of DENV-4 infection in K562 cells (FIG. 6B). Thus, the 9-amino-acid deletion in the Fc $C_H2$ region is responsible for abrogating ADE of DENV replication.

Cross-reactive IgG 1A5 up-regulated DENV infection in monocyte-derived cells in vitro and ADE activity varied widely among DENV serotypes, possibly reflecting amino acid variations in antibody binding site. This possibility was explored with DENV-4 antigenic variants of IgG 1A5 (Goncalvez, A. P. et al. 2004 *J Virol* 78:12919-12928). A higher level of enhancement was detected in infection with variant DENV-4 v1 containing $Leu_{107}Phe$ substitution, compared to the parental DENV-4. This mutation moderately reduced the IgG 1A5-binding affinity (approx. 10 fold), but there were sufficient immune complexes to facilitate infection of Fc receptor-bearing cells. The IgG 1A5-mediated enhancement was not observed with variant DENV-4 v2 containing $Gly_{106}Val$ substitution, which has a low-binding affinity for the antibody (Goncalvez, A. P. et al. 2004 *J Virol* 78:12919-12928). If the mutation in the flavivirus-conserved sequence proves to be a major determinant of an ADE epitope, such a DENV-4 variant can be explored to address vaccine safety related to ADE.

There is heterogeneity of Fc receptors on different human cell lines (Hough, D. W. et al. 1983 *Immunol Lett* 7:85-89). ADE of DENV infection has been detected with K562 cells, which express only the Fcγ RII receptor and U937 cells that express Fcγ RI and Fcγ RII receptors (Littaua, R. et al. 1990 *J Immunol* 144:3183-3186). Fcγ RIIA has been shown to be more effective than Fcγ RI in mediating enhancement of immune complex infectivity (Rodrigo, W. W. et al. 2006 *J Virol* 80:10128-10138). A comparable level of DENV-4 replication enhancement was detected among K562, U937, and Raji-1 cells. The ADE activity was not demonstrable in Raji-1 (DC-SIGN) cells expressing DC-SIGN, which is a DENV receptor found on dendritic cells (Tassaneetrithep, B. et al. 2003 *J Exp Med* 197:823-829). Thus, DENV infection of dendritic cells probably does not require an antibody for enhancement.

There have been attempts to demonstrate ADE of DENV infection in primates by sequential infection with different serotypes (Halstead, S. B. et al. 1973 *J Infect Dis* 128:15-22). Monkeys had significantly higher titers and longer duration of viremia in heterotypic infections with DENV-2 than in primary infections with the same virus. Contradictory results were also obtained, as lower viremia titers were consistently detected in heterotypic infections with DENV-1, 3, or 4 than in primary infections with the same virus. ADE of DENV-2 replication in monkeys was also studied by passive antibody transfer, in which monkeys infused with human dengue immune serum were found to develop viremia titers up to 50 fold higher than control monkeys (Halstead, S. B. 1979 *J Infect Dis* 140:527-533). However, a similar study to demonstrate ADE with a monoclonal or polyclonal antibody in monkeys infected with other DENV serotypes has not been reported in the 28 years since that study.

The DENV infection-enhancing activity of IgG 1A5 in vitro was reproducibly demonstrated in juvenile monkeys. Compared to the earlier ADE study in monkeys infected with DENV-2 at a dose of 1000 and 10,000 PFU following passive transfer with a dilution of human dengue immune serum (Halstead, S. B. 1979 *J Infect Dis* 140:527-533), monkeys in the current study were passively transferred with a range of sub-neutralizing IgG 1A5 dilutions and infected with 10 FFU (100 $MID_{50}$) of DENV-4. Infection enhancement of up to 100-fold in viremia titer was detected, compared to the 50-fold increase in viremia titer described in the earlier study. It is significant that ADE was detected with a different DENV serotype and a considerable range of antibody concentrations. Further, the peak viremia titers were detected on days 5-6 in both studies. It is probably also significant that peak viremia was detected around the time when a patient's illness may progress to DHF.

In previous sequential DENV infections, only one in 118 monkeys appeared to have developed dengue illness that was possibly due to ADE (Halstead, S. B. et al. 1973 *J Infect Dis* 128:15-22). It was not surprising that monkeys in the current study, while experiencing ADE of DENV replication, did not become ill. Prospective studies in humans have suggested a correlation between higher viremia titers than attained by rhesus monkeys and increased risk of severe dengue in second, heterotypic DENV infections (Endy, T. P. et al. 2004 *J Infect Dis* 189:990-1000; Vaughn, D. W. et al. 2000 *J Infect Dis* 181:2-9). This conclusion, however, has not been completely supported in view of recent studies showing that the infection-enhancing activity detected with pre-illness sera in vitro did not correlate with increased viremia titers and disease severity in subsequent infection with DENV-2 or DENV-3 (Endy, T. P. et al. 2004 *J Infect Dis* 189:990-1000; Laoprasopwattana, K. et al. 2005 *J Infect Dis* 192:510-519). Differences in DENV serotype or even strain might be a factor in ADE and dengue severity (Endy, T. P. et al. 2004 *J Infect Dis* 189:990-1000; Vaughn, D. W. et al. 2000 *J Infect Dis* 181:2-9).

It is possible that dengue and its severe DHF/DSS may be a pathogenic course unique to humans. The rapid course in the development of DHF or DSS and its reversible nature, if properly managed, would suggest immunopathogenic elements involving cytokines and other vascular permeability mediators (Kurane, I. & Ennis, F. E. 1992 *Semin Immunol* 4:121-127). In addition to increased viral replication attributed to ADE, interactions between the immune complex and Fc R might also trigger an array of effector cell functions, each with its distinct signaling pathway (Mahalingam, S. & Lidbury, B. A. 2002 *Proc Natl Acad Sci USA* 99:13819-13824). Others have presented a hypothesis linking severe DHF/DSS and cytotoxic T lymphocytes involved in the clearance of DENV-infected monocytes (Kurane, I. & Ennis, F. E. 1992 *Semin Immunol* 4:121-127). According to this model, activated effector cells lyse target monocytes to produce cytokines and other mediators, leading to increased vascular permeability and plasma leakage. It remains speculative which of these immunologically-induced processes would critically affect the outcome of the infection.

ADE has also been attributed to the increased virulence, known as early death, in mice passively administered certain monoclonal antibodies followed by infections with other flaviviruses, such as Japanese encephalitis virus (Kimura-Kuroda, J. & Yasui, K. 1988 *J Immunol* 141:3606-3610) and yellow fever virus (Gould, E. A. & Buckley, A. 1989 *J Gen Virol* 70:1605-1608). Similarly, feline infectious peritonitis virus (FIPV), a coronavirus, causes often fatal infectious peritonitis in cats. ADE of FIPV infection has been shown to be FcR-mediated by neutralizing monoclonal antibodies in vitro (Olsen, C. W. et al. 1992 *J Virol* 66:956-965). Clinically significant human immunodeficiency virus infection may also involve ADE through binding of its immune complex to Fc R or to complement component C1, which in turn reacts with C1q receptor on the cell surface (Fust, G. (1997) *Parasitology* 115(Suppl):S127-S140). Increased uptake of immune complexes and virus infection in C1q-bearing cells, including monocytes/macrophages and epithelial cells, may also account for the rapid fatality of Ebola virus infection (Takada, A. et al. 2003 *J Virol* 77:7539-7544).

Significantly, a 9-amino-acid deletion near one of the key structures in humanized antibody IgG 5H2 was identified that completely abrogated the enhancing activity. The deletion did not alter the antibody neutralizing activity in vitro. The deletion was generated as a result of altered mRNA splicing by a fortuitously-introduced A1058G substitution in the antibody-expressing plasmid. The alternative splicing has been verified by plasmid construction and analysis of variant antibodies. This finding has important implications for the design and construction of antibodies for clinical applications. Alterations of the sequence in the Fc region affecting Fcγ R binding would be expected to affect other effector cell functions, such as antibody-dependent cellular cytotoxicity, and complement pathways, which play a role in viral clearance and that bridge innate and adaptive immune responses. Evidence suggests that antibodies reactive to the nonstructural protein NS1 of DENV and other flaviviruses can protect against infection through complement-dependent cytotoxicity (Falgout, B. et al. 1990 *J Virol* 64:4356-4363). Contributions of the E-specific antibodies to host defense through the complement pathway are less clear. Recent genetic evidence indicates that a humanized monoclonal antibody against West Nile virus (WNV) and its Fc variants were protective against WNV infection in complement C1q- or Fcγ R-deficient mice (Oliphant, T. et al. 2005 *Nat Med* 11:522-530). One interpretation is that the neutralizing activity of antibody plays a far more important role than the antibody-mediated effector functions.

The example below describes in greater detail some of the materials and methods used in Example 1.

EXAMPLE 2

Cultured Cells

Simian Vero cells and mosquito C6/36 cells were grown in Minimum Essential Medium (MEM). Human erythroleukemic K562 cells were grown in Iscove medium, myelomonocytic U937, Raji-1 (a B-cell line) and its derived Raji-1 (DC-SIGN) cells were grown in Advanced RPMI 1640 medium and 293 T cells were cultured in Dulbecco's Modified Eagle Medium. All media were supplemented with 10% fetal bovine serum (FBS), 0.05 mg/ml gentamycin, and 2.5 units/ml fungizone. Mammalian cells were propagated at 37° C. and C6/36 cells at 32° C. Media were purchased from Invitrogen and cells from American Type Culture Collection, except for cell lines Raji-1 and Raji-1 (DC-SIGN), which were kindly supplied by Dr. D. Littman, New York University School of Medicine.

Primary Monocytes

Mononuclear cells were separated from whole blood of rhesus monkeys by Ficoll-Hypaque gradient centrifugation, washed and resuspended in phosphate buffered saline (PBS) plus EDTA and 0.5% bovine serum albumin (BSA). Monocytes were magnetically labeled with CD14 MicroBeads non-human primate (MACS®) and retained in a magnetized column. After washing, CD14+ cells were eluted and resuspended in Advanced RPMI 1640 medium plus supplements at $10^5$ cells/ml and then plated in a 24-well plate. After incubation for 2 h at 37° C., non-adherent cells were removed by washing with PBS and the cell monolayers were infected with DENV. The CD14+ monocytes were 85% to 90% pure, as confirmed by immunostaining with FITC-conjugated anti-CD 14 (Miltenyi Biotec, Auburn, Calif.).

DENV Stocks

All four DENV serotypes were used in this study: DENV-1 (Hawaii prototype); DENV-2 (New Guinea B); DENV-3 (H87); DENV-4 (H241 and 814669). Each virus stock was prepared from infected C6/36 cells grown in VP-SFM medium. After removal of cell debris by centrifugation, the supernatant was stored at −80° C., after which the viral titer was determined.

Analysis of ADE In Vitro

The multiplicity of infection (MOI) for each DENV was adjusted to produce a baseline level of approximately 3 $\log_{10}$ focus-forming units (FFU)/ml in the supernatant of K562 cells 4 days after infection. For flow cytometry, cells were infected with DENV in the presence of varying concentrations of test antibody or DENV sero-negative human IgG as a control essentially as described (Guy, B. et al. 2004 *Vaccine* 22:3563-3574). Briefly, approximately $4\times10^5$ cells were suspended in 100 µl of maintenance medium (Iscove medium for K562 cells or Advanced RPMI 1640 for other cells, all supplemented with 2% FBS). Equal aliquots (50 µl) of serially diluted antibody or sero-negative IgG and the DENV inoculum were mixed. After 1 h incubation at 37° C. under 5% $CO_2$, the virus-antibody mixture was added to monocytes and incubated for an additional 1.5 h. The infected monocytes were rinsed with maintenance medium and centrifuged. Fresh maintenance medium was added and the cells were transferred to a 24-well plate. After a 4-day incubation, the virus in the medium was titered by focus assay. For flow cytometry, the increase of DENV-infected cells was determined 1 or 2 days after infection.

Flow Cytometry

DENV-infected cells were transferred to an Eppendorf tube and centrifuged to remove the supernatant. Fixation, permeabilization and intracellular fluorescence labeling were performed essentially as described (Guy, B. et al. 2004 *Vaccine* 22:3563-3574). For labeling, cells were incubated with dengue complex-reactive monoclonal antibody 8705 (Chemicon, Temecula, Calif.) and then labeled with anti-mouse immunoglobulins/FITC (DakoCytomation). Cells were resuspended in Dulbecco's PBS plus 0.2% BSA and subjected to flow cytometry analysis using a Becton Dickinson FACScan instrument. Data were analyzed using FLOWJO software (Tree Star, Ashland, Oreg.).

ADE of DENV Infection in Rhesus Monkeys

Five groups of three monkeys each were infused intravenously with IgG 1A5 at a dose of 18, 6, 2, 0.67 and 0.22 mg/kg in PBS and another group of three monkeys received PBS only. One day later, the concentration of IgG 1A5 in monkey sera was determined by ELISA with a standard curve generated using a purified preparation of IgG 1A5 in PBS (Men, R. et al. 2004 *J Virol* 78:4665-4674). The plaque reduction neutralization test (PRNT) was performed to determine the serum IgG 1A5 $PRNT_{50}$ titer. All monkeys were challenged with 100 monkey infectious $dose_{50}$ ($MID_{50}$) (equivalent to 10 FFU) of DENV-4 in 0.5 ml by the subcutaneous route. DENV-4 strain 814669 propagated in Vero cells was used. Serum samples from each monkey were collected daily for the next 10 days and again at 2, 4, 6 and 8 weeks for analysis of viremia and antibody.

Quantitative Analysis of DENV-4 Viremia and Sero-Response in Monkeys

For assay of FFU, serial dilutions of serum samples in MEM plus 0.05% BSA were added to Vero cell monolayers in 24-well plates and incubated for 1 h at 37° C. A medium overlay containing 10% gum tragacanth (Sigma) was added and infected cells were incubated at 37° C. for 3 days. The detection limit was 0.7 $\log_{10}$ FFU/ml. The DENV-4 titer in monkey sera was also determined by real-time, quantitative RT-PCR (qRT-PCR). DENV-4 M specific primer pairs were $_{843}$CTCTTGGCAGGATTTATGGCTTA$_{865}$ (SEQ ID NO: 20) and $_{906}$CAAAGAAGACAGTTCGCTGGATT$_{883}$ (SEQ ID NO: 21). The probe was $_{867}$ATGATTGGGCAAA-CAG$_{882}$ (SEQ ID NO: 22) labeled with 6-carboxyfluorescein at the 5' end and a minor groove binder plus non-fluorescent quencher at the 3' end. Viral RNA was isolated from 100 μl of serum with the QIAmp Viral RNA Mini Kit (Qiagen). RT-PCR was performed by using the TaqMan One-Step RT-PCR Kit (Applied Biosystems) in an ABI PRISM® 7900HT Sequence Detection System. DENV-4 strain 814669 was used to generate a standard curve using 10-fold dilutions of RNA isolated from a known amount of virus (6.3 $\log_{10}$ FFU/ml), covering a 5 $\log_{10}$ dynamic range (6.3 $\log_{10}$ to 1.3 $\log_{10}$ FFU/ml). The amount of infectious RNA transcripts per reaction corresponded to the known FFU per reaction and is expressed as equivalent FFU (Eq FFU). The detection limit was 0.8 $\log_{10}$ Eq FFU/ml. DENV-4 cDNA concentration curves were also generated and the conversion factor was approximately 0.034 Eq FFU per copy. Radio-immunoprecipitation was used to semi-quantify the anti-NS1 antibodies present in monkey sera 2, 4 and 6 weeks after challenge, as an independent measurement of DENV-4 infection as described previously (Falgout, B. et al. 1990 *J Virol* 64:4356-4363).

Construction of IgG 1A5 Fc Variants

Mutations in the Fc region of IgG 1A5 were generated in the pFab CMV expression vector by overlap extension PCR (Men, R. et al. 2004 *J Virol* 78:4665-4674). Briefly, substitutions of $C_{1348} \rightarrow G$, $G_{1356} \rightarrow T$, and $C_{1359} \rightarrow T$ according to the numbering system of Takahashi, N. et al. 1982 *Cell* 29:671-679 were introduced using the Bsa I site at position 1334 near the C-terminus of $C_H2$ of IgG 1A5 to generate IgG 1A5 ΔA containing amino-acid substitutions at 327, 330 and 331 according to the numbering system of Armour, K. L. et al. 1999 *Eur J Immunol* 29:2613-2624. Variant IgG 1A5 ΔB containing the substitution of amino acids 233-236 was created by replacing ACCGGTCGC (SEQ ID NO: 23) for TGAACTCCTGGG$_{1075}$ (SEQ ID NO: 24) (to generate three amino-acid substitutions and a deletion near the N-terminus of $C_H2$). These replacements generated an AgeI (ACCGGT (SEQ ID NO: 25)) site for mutant construction. Variant IgG 1A5 ΔC was generated by combining ΔA and ΔB substitutions described above by replacement of the SacII-BsrGI fragment. To generate IgG 1A5 ΔD, containing the 9 amino acid deletion, two DraIII sites at positions 1053 and 1080 were first introduced to remove the intervening 27 nucleotides and then the original splice site sequence was restored with a QuickChange® Site-Directed Mutagenesis Kit (Stratagene, La Jolla, Calif.).

Sequence Analysis of mRNA

Total RNA was isolated from transfected 293 T cells or transformed Chinese hamster ovary (CHO) cells using TRIzol™ Reagent (Invitrogen). First-strand cDNA was synthesized with the Superscript II RT kit (Invitrogen) and the anti-sense primer $_{1806}$TTTACCCGGAGACAGG-GAGAGG$_{1785}$ (SEQ ID NO: 26) at the 3' end of the IgG $C_H3$ domain. For sequencing, the DNA fragment covering the $C_H1$, hinge, $C_H2$ and $C_H3$ domains of IgG was amplified using appropriate primers and Ampli-Taq DNA polymerase (Perkin-Elmer). Sequence assembly and analysis were performed using Sequencher™ v4.5 (Gene Codes Corporation).

Expression and Purification of IgGs

IgG 1A5 and IgG 5H2 ΔD, derived from chimpanzee Fabs, were prepared from transformed CHO cells by a large-scale production method (Goncalvez, A. P. et al. 2004 *J Virol* 78:12910-12918; Men, R. et al. 2004 *J Virol* 78:4665-4674) (Kemp Biotechnology, Gaithersburg, Md.). Plasmids of parental or variant IgGs were also prepared by transient transfection of 293 T cells and the products were affinity-purified on a protein A column (Kemp Biotechnology, Gaithersburg, Md.).

Examples 3 and 4 demonstrate the epitope determinants of a DENV-4-specific MAb and protection against DENV-4 challenge in mice and rhesus monkeys by passively transferred humanized antibody.

EXAMPLE 3

Epitope Determinants of a Chimpanzee Dengue Virus Type 4 (DENV-4)-Neutralizing Antibody and Protection Against DENV-4 Challenge in Mice and Rhesus Monkeys by Passively Transferred Humanized Antibody Chimpanzee Fab-derived monoclonal antibody (MAb) IgG 5H2 is specific for dengue type 4 virus (DENV-4) and able to neutralize the virus at a high titer in vitro. The epitope detected by the antibody was mapped by isolation and sequencing of antigenic variants of the virus. One variant contained a $Lys_{174}$-Glu substitution and another contained a $Pro_{176}$-Leu substitution in domain I of DENV-4 envelope protein (E). These closely spaced mutations reduced binding affinity to the antibody by 18 to >100 fold. Humanized IgG 5H2 produced from an expression vector has been shown to be a variant, containing a 9-amino-acid deletion in the Fc region which completely ablates the antibody-dependent enhancement activity of DENV replication in vitro. The variant MAb, termed IgG 5H2 ΔD, is particularly attractive for exploring its protective capacity in vivo. Using the mouse dengue encephalitis model, passive transfer of IgG 5H2 AD at approximate 20 μg/mouse afforded 50% protection of suckling mice against challenge with 25 lethal $dose_{50}$ of mouse neurovirulent DENV-4 strain H241. Passive transfer of antibody to monkeys was conducted to demonstrate proof of concept for protection against DENV challenge. Monkeys that received 2 mg/kg of IgG 5H2 A/D were completely protected against 100 monkey infectious $dose_{50}$ ($MID_{50}$) (10 focus-forming units) of DENV-4, as indicated by the absence of viremia and sero-conversion. A DENV-4 escape mutant that contained the $Lys_{174}$-Glu substitution identical to that found in vitro was isolated from monkeys challenged with $10^6$ $MID_{50}$ of DENV-4. This substitution was also present in all naturally occurring isolates belonging to DENV-4 genotype III that had emerged during 1997-1999 in Bangkok, Thailand. These studies have important bearings on antibody-mediated prevention of dengue infection.

Introduction

The four dengue virus serotypes (DENV-1 to DENV-4) cause more morbidity in humans than any other arthropod-borne flaviviruses (Monath, T. P. 1994 *Proc Natl Acad Sci USA* 91:2395-400). Up to 100 million DENV infections occur every year, mostly in tropical and subtropical areas where the vector mosquitos, principally *Aedes aegypti* and *A. albopictus*, are present. Dengue illnesses range from mild fever to severe dengue hemorrhagic fever (DHF) and dengue shock syndrome (DSS), which has a high fatality rate in children. Most severe dengue (greater than 90%) occurs in patients re-infected with DENV infection of a serotype different from the primary infection (Guzman, M. G. et al. 1987 *Bull Pan Am Health Organ* 21:270-9; Sangkawibha, N. 1984 *Am J Epidemiol* 120:653-69). Antibody-dependent enhancement (ADE) of DENV replication has been proposed as an underlying pathogenic mechanism of severe DHF/DSS (Halstead, S. B. 1970 *Yale J Biol Med* 42:350-62). A safe and effective vaccine against dengue is still not available.

Early studies of DENV infections in human volunteers showed that homotypic immunity against the same serotype is life-long, but heterotypic immunity against other serotypes lasts only months (Sabin, A. B. 1952 *Am J Trop Med Hyg* 1:30-50). Since antibodies provide the first line of host defense against infection, type-specific immunity afforded by antibody may contribute significantly to long-term protection. Antigenic differences exist among strains of the same serotype (Henchal, E. A. et al. 1986. *Am J Trop Med Hyg* 35:393-400). DENV variants that form defined genotypes, in some cases with restricted geographic distribution, have been isolated during and between epidemics (Lanciotti, R. S. et al. 1997 *J Gen Virol* 78 (Pt 9):2279-84; Rico-Hesse, R. 2003 *Adv Virus Res* 59:315-41). Molecular epidemiologic analysis of DENV-4 showed that these virus variants probably arose and disappeared due to high mutation rates associated with adaptive evolution in the transmission between mosquito and human hosts (Bennett, S, N. et al. 2003 *Mol Biol Evol* 20:1650-8; Klungthong, C. et al. 2004 *Virology* 329:168-79).

The three-dimensional (3-D) structure of the flavivirus envelope glycoprotein (E) was first reported for the tick-borne encephalitis virus (Rey, F. A. et al. 1995. *Nature* 375: 291-8). The 3-D structures of DENV-2 E and DENV-3 E have also become available recently (Modis, Y. et al. 2003 *Proc Natl Acad Sci USA* 100:6986-91; Modis, Y. et al. 2005 *J Virol* 79:1223-31). Flavivirus E proteins assume a similar flat, elongated dimeric architecture. Each E subunit folds itself into three structurally distinct domains, termed domains I, II and III. Domain 1 is organized into an 8-stranded central (3-barrel structure. The two large loops that connect strands of domain I form the elongated domain II, which contains the flavivirus-conserved fusion peptide at its distal end. Domain III can independently fold into an immunoglobulin-like module and is also connected to domain I.

Studies on functional activities and binding specificities of mouse monoclonal antibodies (MAbs) have revealed the antigenic structure of flavivirus E that is remarkably similar to the 3-D structure (Guirakhoo, F. et al. 1989 *Virology* 169:90-9; Heinz, F. X. 1986 *Adv Virus Res* 31:103-68; Mandl, C. W. et al. 1989 *J Virol* 63:564-71; Roehrig, J. T. et al. 1998 *Virology* 246:317-28). Antibodies that recognize epitopes involving determinants in domain II are broadly cross-reactive, but weakly to non-neutralizing. These antibodies can affect virus-cell membrane fusion and the structural integrity of domain II for antibody binding is pH-sensitive (Guirakhoo, F. et al. 1989 *Virology* 169:90-9). Antibodies reactive to domain III are mostly type- or subtype-specific, efficient neutralizers of viral infectivity and block viral attachment, but not fusion (Nybakken, G. E. et al. 2005 *Nature* 437:764-9; Roehrig, J. T. et al. 1998 *Virology* 246:317-28). Only relatively few MAbs reactive to domain I epitopes on dengue virus E have been isolated and characterized (Roehrig, J. T. et al. 1998 *Virology* 246:317-28; Serafin, I. L. et al. 2001 *Arch Virol* 146:2469-79). The functional role of the domain I structure remains poorly understood.

Murine MAbs that are highly neutralizing against several flaviviruses in vitro have been shown to be also highly protective in animal models (Brandriss, M. W. et al. 1986 *J Gen Virol* 67 (Pt 2):229-34; Kimura-Kuroda, J. 1988 *J Immunol* 141:3606-10). However, these mouse MAbs are not directly useful for clinical application, because of their immunogenicity in humans. MAbs from chimpanzees infected with multiple dengue virus serotypes were identified. Humanized MAb IgG 1A5 recognizes sequences in the fusion loop in domain II and is cross-reactive with dengue and most other flaviviruses (Goncalvez, A. P. et al. 2004 *J Virol* 78:12910-8; Goncalvez, A. P. et al. 2004 *J Virol* 78:12919-28). MAb IgG 5H2 is type-specific and highly efficient for neutralization of DENV-4 in vitro (Men, R. et al. 2004 *J Virol* 78:4665-74).

In the course of constructing these humanized MAbs, an IgG 5H2 variant that had a 9-amino-acid deletion in the Fc region was isolated, resulting from an alternative splicing due to a nucleotide substitution in expression plasmid (Goncalvez, A. P. et al. 2007 *Proc Natl Acad Sci USA* 104:9422-27). The variant MAb, designated as IgG 5H2 ΔD hereafter, and its full-length IgG 5H2 neutralized DENV-4 equally efficiently. The ADE activity of DENV replication mediated by IgG 5H2 ΔD was abrogated. Such an antibody is particularly attractive for further exploring its potential for clinical application. In this study, the epitope determinants of the DENV-4-specific MAb have been determined by isolation and sequence analysis of antigenic variants. Protection against DENV-4 challenge was demonstrated in mice and rhesus monkeys by passively transferred humanized antibody.

DENV-4 Antigenic Variants of Chimpanzee Antibody Fab 5H2

Figure 7A:
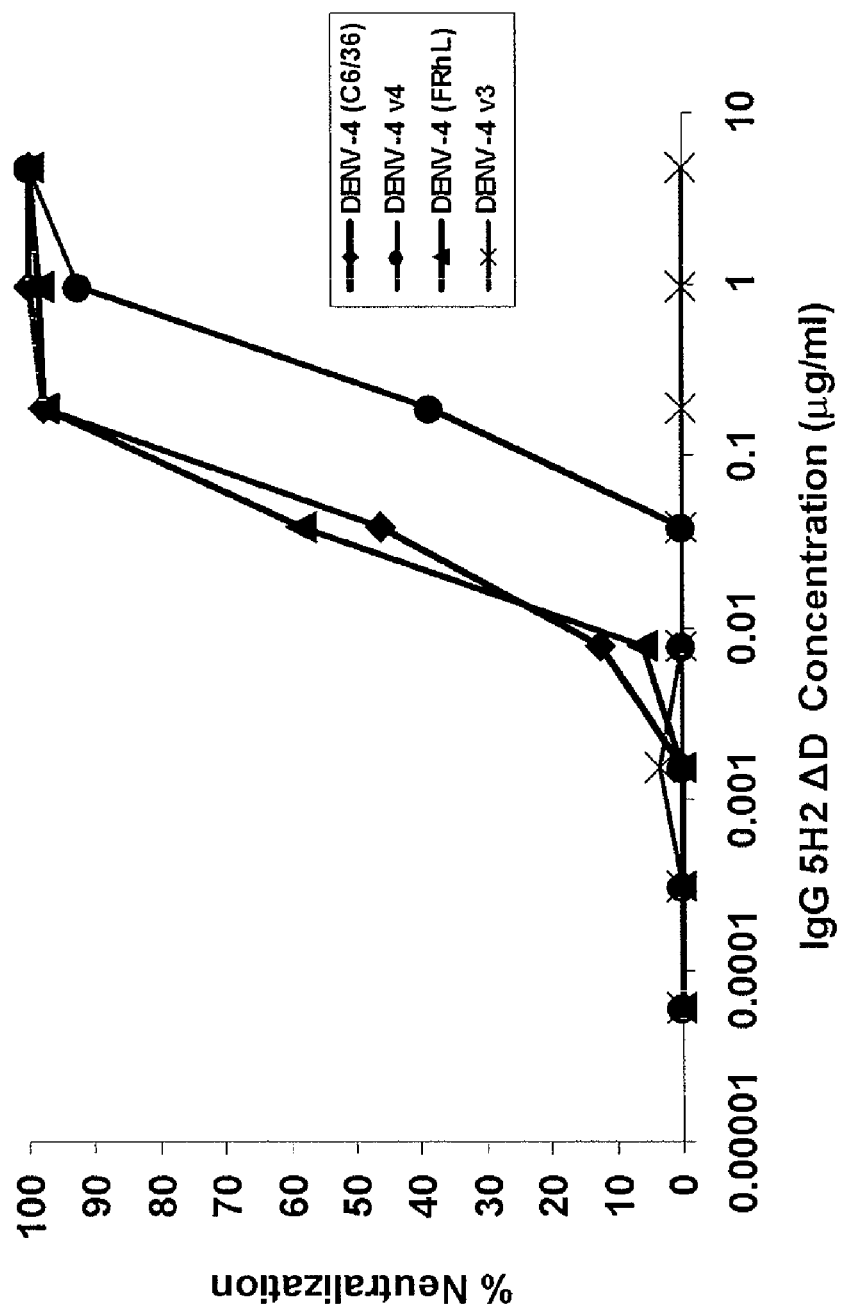
FIG. 7. Neutralization assay of IgG 5H2 ΔD against DENV-4 parental viruses and antigenic variants using IgG 5H2 ΔD in vitro (A). Growth curves of DENV-4 antigenic variants and parental viruses in C6/36 cells (B). The moi was 0.1.

DENV-4 (FRhL) and DENV-4 (C6/36) were both used for selection of antigenic variants of Fab 5H2. An antigenic variant, designated DENV-4 v3, was recovered from DENV-4 (FRhL) after three cycles of neutralization and propagation. A second antigenic variant, designated DENV-4 v4, was selected from DENV-4 (C6/36) also after three cycles of neutralization and propagation. Using DENV-4 v3 for the neutralization assay, Fab 5H2 had a $PRNT_{50}$ titer greater than 20 µg/ml. Using DENV-4 v4 for neutralization, the Fab had a $PRNT_{50}$ titer of approximately 5 µg/ml, compared with $PRNT_{50}$ titers of 0.3-0.5 ug/ml using their parental viruses. When both parental viruses were used, IgG 5H2 and its derived IgG 5H2 ΔD had similar titers of 0.03-0.05 µg/ml. IgG 5H2 ΔD completely neutralized DENV-4 v3 ($PRNT_{50}$>10 µg/ml) and had a $PRNT_{50}$ titer of approximately 0.5 µg/ml against DENV-4 v4 (FIG. 7A).

Figure 7B:
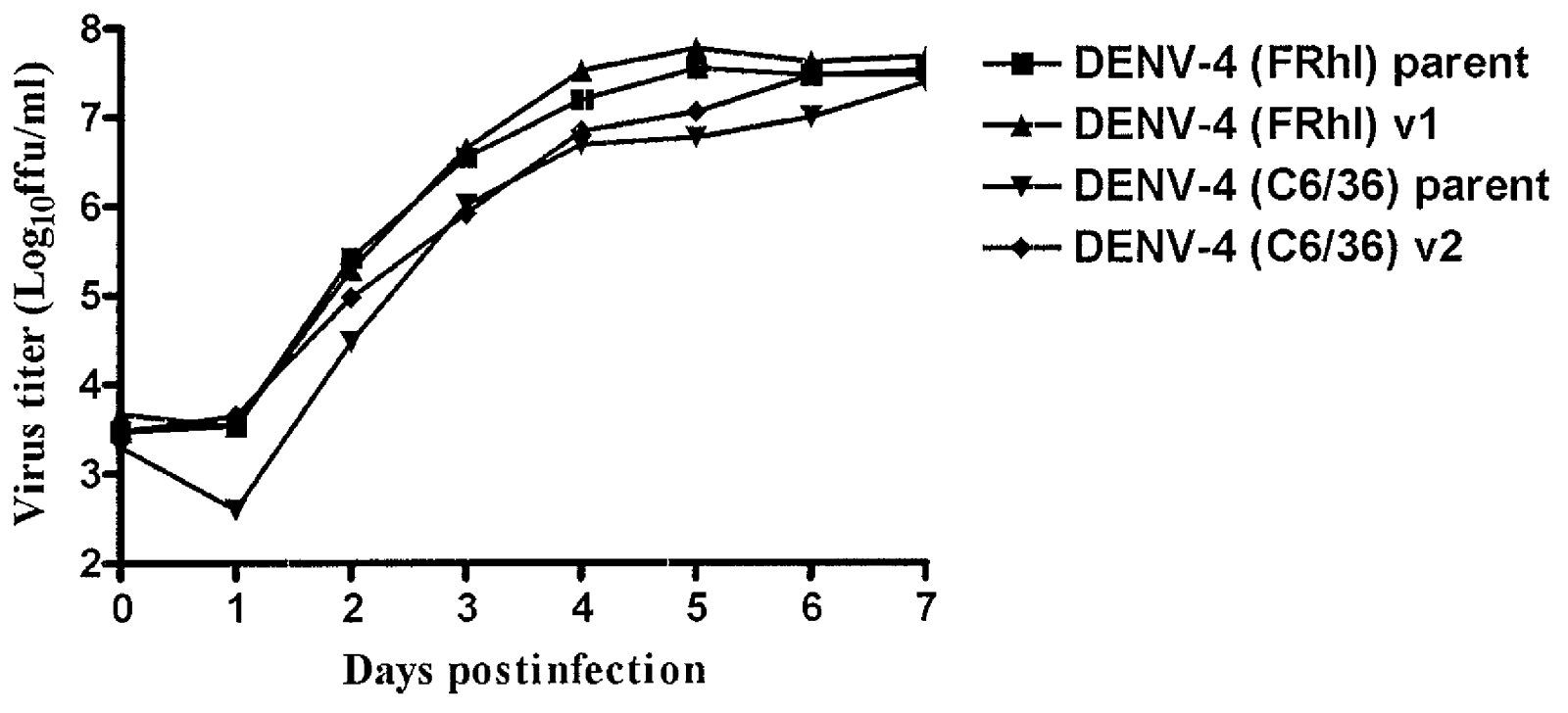

The growth properties of DENV-4 variants and their parental viruses were compared. Parental DENV-4 (FRhL) produced a small plaque morphology compared with parental DENV-4 (C6/36) on Vero cells. The plaque size of each of the variants was similar to its parental virus. The growth rate of each variant was similar to its parental virus when analyzed in C6/36 cells and in Vero cells. FIG. 7B shows that each of these viruses grew to a similar titer in C6/36 cells in a 7-day period. The growth curves of the variants and their parent viruses were also similar in Vero cells. Clearly, the mutations in the variants did not confer a growth advantage compared to wild type DENV-4.

Sequence Analysis of DENV-4 Antigenic Variants

The amino acid change in the C-prM-E structural protein region in each of the variants was determined in order to map the epitope on DENV-4 E that bound to Fab 5H2. Parental DENV-4 (C6/36) and DENV-4 (FRhL) differed by a substitution of Glu for Gln at position 363 in E, possibly resulting from passage and adaptation for growth in FRhL cells. DENV-4 v3 acquired a single A-to-G mutation at nucleotide 1458 that resulted in substitution of Glu for Lys at position 174 in E. In contrast, DENV-4 v4 contained a C-to-T mutation at nucleotide 1465 that produced a substitution of Leu for Pro at position 176 in E. The close spacing of these mutations indicates that $Glu_{174}$ and $Leu_{176}$ represent important determinants of the Fab 5H2-reactive epitope. $Lys_{174}$ of DENV-4 E is unique among the dengue viruses. $Pro_{176}$ is present in DENV-3, but a Thr occupies this position in DENV-1 and DENV-2. There is considerable variation at each of these positions among the major flaviviruses, as seen in the alignment of the amino acid sequences at and surrounding these mutations (FIG. 8A). In the 3-D structure, these closely spaced amino acids are located near or within the three-amino acid loop between $G_0$ and $H_0$ β-strands in domain I (FIG. 8B). The loop region is exposed on the E surface, consistent with its accessibility for antibody binding (FIG. 8C).

Binding Affinity of Fab 5H2 and IgG 5H2 ΔD for DENV-4

An ELISA was performed to semi-quantify the binding affinities of Fab 5H2 and its derived IgG 5H2 ΔD for parental and variant DENV-4 (Table 5). Binding of Fab 5H2 to the parental viruses reached a maximum at about 0.1 μg/ml. The half-maximal binding values (apparent binding affinity, termed ELISA Kd) was 0.36 nM for DENV-4 (FRhL) and 0.21 nm for DENV-4 (C6/36). Under the same conditions, the ELISA Kd for DENV-4 v3 was >100 nM, a reduction of greater than 100 fold and the ELISA Kd for DENV-4 v4 was 3.7 nM, a reduction of approximately 18 fold. The affinity for binding of IgG 5H2 ΔD to these viruses was also determined. There was only approximately 2 fold reduction of binding affinity for DENV-4 v4, compared to its parental virus. On the other hand, binding affinity of IgG 5H2 ΔD to DENV-4 v3 was reduced greatly, compared to its parent. In each case, reduction of antibody binding affinity correlated with increased resistance to antibody neutralization.

TABLE 5

Relative binding affinity of Fab 5H2 and IgG 5H2 ΔD as determined by ELISA

| Virus | Fab 5H2 | | IgG 5H2 ΔD | |
|---|---|---|---|---|
| | Kd (nM) | Fold Reduction | Kd (nM) | Fold Reduction |
| DENV-4 (FRhL) | 0.36 | | 0.23 | |
| DENV-4 v3 | >100 | >100 | >100 | >100 |
| DENV-4 (C6/36) | 0.21 | | 0.14 | |
| DENV-4 v4 | 3.71 | 17.7 | 0.32 | 2.29 |

Kd values of parental DENV-4 and derived mutants were determined from the concentrations giving 50% maximal binding in affinity ELISA assay. Two to three separate binding experiments were performed for each virus to obtain the average value.

ADE and Other Functional Properties of the DENV-4 Specific Epitope

Figure 9A:
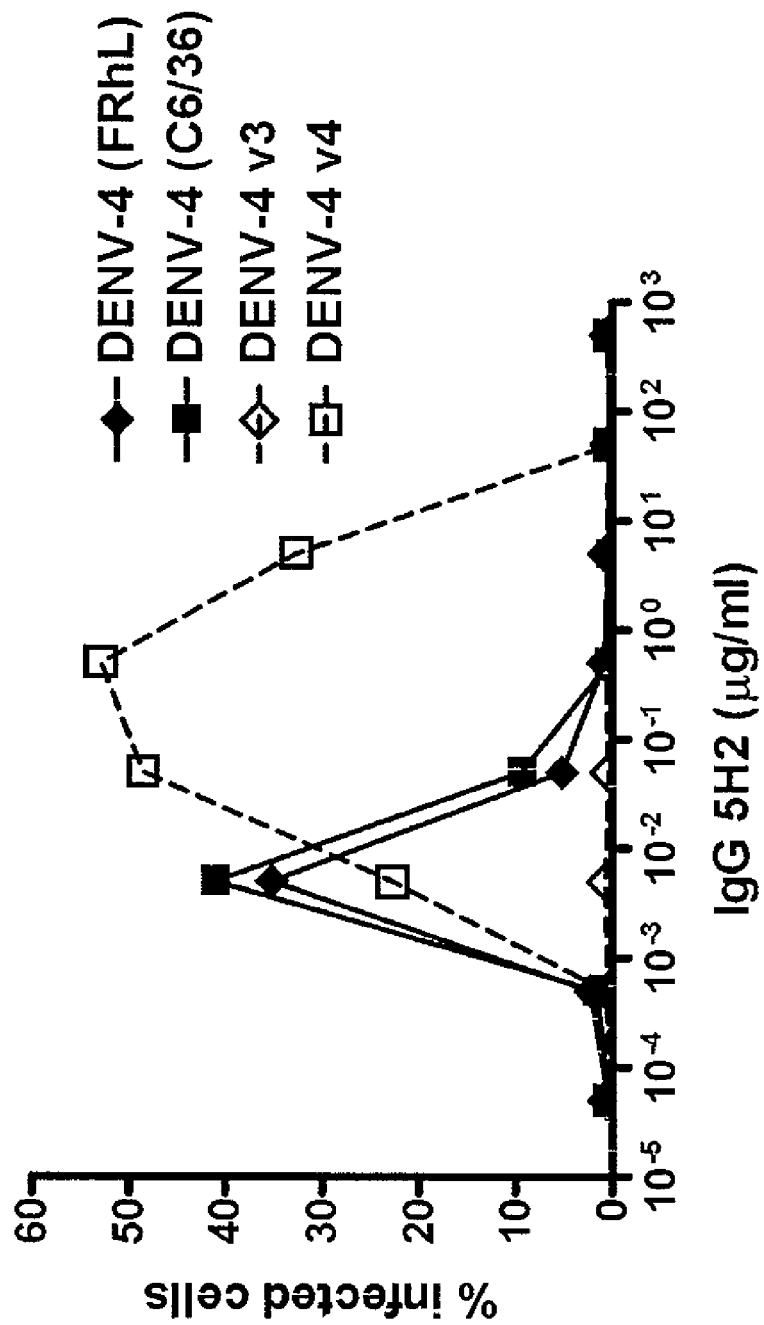
FIG. 9. ADE of the DENV-4 specific epitope and neutralization of DENV-4 by IgG 5H2 ΔD before or after adsorption to Vero cells. Comparison of ADE activity of parental DENV-4 and its derived antigenic variants in K562 cells mediated by full-length IgG 1A5. Percent of cells infected with DENV-4 was determined by flow cytometry (A). A constant amount of virus was tested against various dilutions of IgG 5H2 ΔD (B).

It was shown that sequence variations at the antibody binding sites were responsible for the difference in ADE activities (Goncalvez, A. P. et al. 2007 Proc Natl Acad Sci USA 104: 9422-27). This finding was further tested by comparison of IgG 5H2-mediated enhancing activities against DENV-4 parental viruses and their derived antigenic variants v3 and v4, which had reduced binding affinities. As predicted, IgG 5H2 enhanced the infection of parental viruses, but not low-affinity DENV-4 v3 in K562 cells (FIG. 9A). In contrast, enhancement of infection by DENV-4 v4 was detected over a broad range of IgG 5H2 concentrations (50-0.005 ug/ml), reminiscent of the enhancement pattern mediated by cross-reactive MAb IgG 1A5. This analysis showed that the type-specific IgG 5H2 epitope also mediated ADE and its activity depended on the binding affinity of the antibody-virus complex.

Figure 9B:
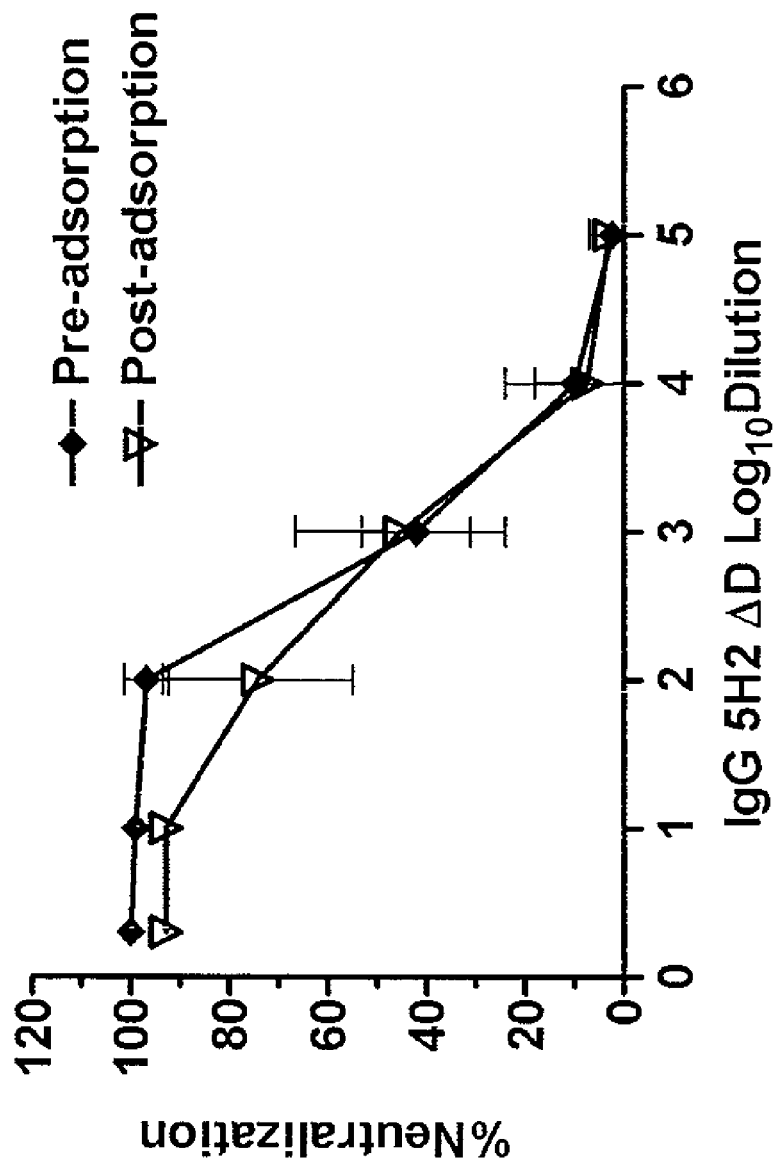

The conformational dependency of the Fab 5H2-reactive epitope was also investigated. While sodium dodecyl sulphate (SDS) treatment of DENV-4 E had no apparent effect on Fab 5H2 antibody binding, UV-irradiation or treatment with 2-β-mercapto-ethanol completely abolished Fab 5H2 binding of DENV-4 as determined by ELISA or western blot analysis. Hemagglutination inhibition assay showed that the HI titer of IgG 5H2 AD ($PRNT_{50}$ titer at 1:9,000) was <4, whereas the control sera from DENV-4 infected monkeys ($PRNT_{50}$ titer at 1:600) was greater than 128 using DENV-4 as antigen. These results are consistent with the notion that the integrity of the Fab 5H2-reactive epitope on DENV-4 E is conformationally maintained and not involved in HI reactivity. To determine whether IgG 5H2 ΔD binding blocked viral adsorption, a comparative neutralization assay was performed on DENV-4 before and after adsorption to the Vero cells (FIG. 9B). IgG 5H2 ΔD was nearly equally efficient for neutralization of DENV-4, suggesting binding of the antibody did not apparently block adsorption of DENV-4 to the cells.

Protection Against DENV-4 Infection of Mice

Mice intracerebrally infected with a mouse-adapted, neurovirulent dengue virus develop encephalitis and eventually die without intervention. The mouse dengue fatal encephalitis model was initially employed to analyze the protective efficacy of IgG 5H2 ΔD against DENV-4 infection in vivo. Table 6 shows that the survival rates of mice after challenge with neurovirulent DENV-4H241 depended on the dose of IgG 5H2 ΔD transferred. Nearly all mice in the control group and the group that received the lowest dose (4 μg/mouse) of antibody succumbed to DENV-4H241 infection (survival rates 10-13%). The survival rate was 92% for the group that received 92 μg of the antibody and 46% for the group that received 20 μg of antibody after challenge. The amount of IgG 5H2 ΔD that afforded 50% protection of mice was approximately 20 μg per mouse.

TABLE 6

Protection of suckling mice by passive transfer of IgG 5H2 ΔD against challenge with a neurovirulent DENV-4

| Mice (No./group) | IgG 5H2D (ug/mouse) | No. of mice Surviving (%) |
|---|---|---|
| 8 | 0 | 1 (12.5) |
| 10 | 4 | 1 (10.0) |
| 11 | 20 | 5 (45.5) |
| 12 | 92 | 11 (91.7) |

Groups of 3 to 4-day-old suckling mice were inoculated intra-peritoneally with IgG 5H2 ΔD at the dose indicated and then challenged with 25 $LD_{50}$ of neurovirulent DENV-4 H241 24 hours later.
Mice were moribund 20 days after challenge.

Protection of Monkeys by Passive Transfer of Antibody

The amount of DENV used for infection may be critical for analysis of protection by antibody in rhesus monkeys. The monkey infectious dose of the challenge DENV-4 strain was determined in order to better evaluate the protective capacity of neutralizing antibody IgG 5H2 ΔD. Pairs of monkeys were infected with a range of DENV-4 doses (1.0, 0.1, and 0.01 ffu) and sero-conversion was determined 8 to 10 weeks later. The titration result showed that the DENV-4 50% monkey infectious dose ($MID_{50}$) was 0.1 ffu (Table 7).

TABLE 7

Determination of 50% monkey infectious dose of DENV-4 strain 814669

| Monkey | DENV-4 titer (ffu) | Sero-conversion |
|---|---|---|
| RH 665 | 1 | + |
| RH 667 | 1 | + |
| RH 668 | 0.1 | + |
| RH 671 | 0.1 | − |
| RH 687 | 0.01 | − |
| RH 691 | 0.01 | − |

Monkeys were inoculated with 10-fold dilutions of DENV-4 and sero-conversion was determined by IgG ELISA 8 weeks after infection.

In the next experiment, four monkeys that had been given 2 mg/kg of IgG 5H2 ΔD intravenously and two control monkeys that received PBS only were challenged with 100 $MID_{50}$ (10 ffu equivalent) of DENV-4 strain 814669 one day later. Table 8 shows that viremia was detected in one control monkey, lasting for 3 days with peak virus titer at 120 ffu/ml on day 7 and the positive viremia was confirmed by the more sensitive TagMan RT/PCR analysis. Viremia was not detected in samples of the other control monkey, either by direct plaque assay or by PCR assay. Nevertheless, both control monkeys were clearly infected with DENV-4, as each developed NS1 antibody as seen by radio-immunoprecipitation (Table 8). Viremia was not detected in any of the four monkeys that received IgG 5H2 ΔD antibody and were subsequently challenged with DENV-4. Sero-analysis by radio-immunoprecipitation also showed that the NS1 antibody was not detected in the four monkeys (Table 8), indicating that DENV-4 was completely neutralized and its replication was prevented in these monkeys. This study demonstrates proof of principle that passive transfer of antibody IgG 5H2 ΔD protected all four monkeys against DENV-4 infection.

TABLE 8

Protection of monkeys against DENV-4 challenge by passive transferred IgG 5H2D

| Monkey | Antibody Transferred (2 mg/kg) | Viremia (day after challenge) | | Sero-conversion | Protection |
|---|---|---|---|---|---|
| | | Focus assay ffu/ml | RT/PCR Eq. ffu/ml | | |
| H671 | no | 13(6), 120(7), 27(8) | 120(6), 500(7), 550(8) | yes | no |
| H687 | no | nd | nd | yes | no |
| CF7H | yes | nd | nd | no | yes |
| CF7B | yes | nd | nd | no | yes |
| CJ4X | yes | nd | nd | no | yes |
| H742 | yes | nd | nd | no | yes |

Rhesus monkeys were each challenged with 100 $MID_{50}$ of DENV-4 one day after antibody transfer. Viremia titer was analyzed by direct plaque analysis and by RT/PCR (TagMan). Sero-conversion was determined by the presence of anti-NS1 antibodies using radio-immunoprecipitation. Evidence of infection, ie., sero-conversion, was used to assess protection. nd indicates not detected..

Isolation of Antigenic Variants from Monkeys Infected with $10^6$ $MID_{50}$ DENV-4

Since partial neutralization of DENV-4 by Fab 5H2 generated escape mutants in vitro, whether DENV-4 antigenic variants could also be isolated in vivo was studied. Four monkeys that received IgG5H2 ΔD at 0.9 mg/kg by passive transfer and two monkeys that received PBS alone as control were each challenged with $10^6$ $MID_{50}$ of DENV-4 24 hr later. Table 9 shows that viremia was detected for 5-6 days, with the peak titer ranging from 10 to 230 ffu/ml in the control monkeys. Monkeys that received the antibody also developed viremia with similar duration and peak virus titers. One of these monkeys (RH685) showed a delayed onset and short duration of viremia as compared to other monkeys, suggesting the possibility of reduced DENV-4 replication and partial protection by antibody. The result was further supported by sero-analysis using radio-immunoprecipitation. All four monkeys that received antibody by passive transfer, similar to the two control monkeys, developed antibodies against prM and NS1, confirming that there was DENV-4 replication in these monkeys. The monkey with a delayed and minimal viremia developed only a low level of prM and NS1 antibodies compared to other monkeys, confirming attenuated infection.

TABLE 9

Viremia following challenge of $10^6$ $MID_{50}$ DENV-4 in rhesus monkeys passively administered with IgG 5H2 ΔD

| Monkey | IgG 5H2 ΔD (0.9 mg/kg) | Viremia Onset day | Duration (days) | Peak virus titer pfu/ml |
|---|---|---|---|---|
| RH690 | − | 2 | 6 | 230 |
| RH670 | − | 2 | 5 | 10 |
| RH692 | + | 6 | 6 | 80 |
| RH688 | + | 6 | 4 | 200 |
| RH693 | + | 4 | 5 | 210 |
| RH685 | + | 8 | 2 | 10 |

Rhesus monkeys that received IgG 5H2 ΔD (iv) (approximately 300 $PRNT_{50}$/ml) were challenged (sc) with 1 × $10^5$ $MID_{50}$ DENV-4 24 hr later.
Control monkeys that received diluent PBS were similarly challenged.
Monkey serum samples of days 1-12 post-challenge were analyzed for viremia by plaque assay.

The virus present in several viremic samples from passively immunized monkeys was recovered and the sequence in the C-prM-E region was analyzed. A substitution of Glu for $Lys_{174}$ in E was found in the virus recovered from the day 6 serum sample of monkey RH693 and from the day 8 sample of monkey RH688. A substitution of Arg for $Lys_{174}$ was found in the virus recovered from the day 9 samples of monkey 692 and monkey RH688. Both variant viruses were recovered from monkey RH688. Wild type DENV-4 was not recovered from these samples. Significantly, substitution of Glu for $Lys_{174}$ was identical to that found in antigenic variant v3 isolated in vitro.

Discussion

Panels of chimpanzee MAbs have been recovered from infections with multiple dengue virus serotypes by repertoire cloning. DENV-4-specific MAb Fab 5H2 is unique in that it is highly potent for in vitro neutralization of virus isolates from different geographic regions (Men, R. et al. 2004 *J Virol*

78:4665-74). The epitope reactive with antibody Fab 5H2 was determined by isolation and sequencing of antigenic variants of DENV-4. Important sites for binding of Fab 5H2 were localized to amino acids 174 and 176 in E near or within the 3-amino-acid loop between $H_0$ and $G_0$ β-strands in domain I of the 3-D structure. The location of these closely-spaced amino acids on the glycoprotein surface is consistent with their accessibility to antibody binding. There is greater than 40% sequence diversity among dengue and other flaviviruses in the region that includes the 3 amino-acid loop and 5 amino acids flanking each side. The epitope was conformationally dependent, as treatment of DENV-4 with UV irradiation or reducing agent completely destroyed the binding capacity for Fab 5H2. The substitution of Leu for $Pro_{176}$ was a non-conservative change that would have increased the local hydrophobicity of the region surrounding residues 174-178 of E from a mean hydrophobicity score of −6.1 for wild type DENV-4 to −2.3 for variant DENV-4 v4 (Kyte, J. et al. 1982 *J Mol Biol* 157:105-32). The substitution of Glu for $Lys_{174}$ was a charged amino acid change that would have increased the local hydrophobicity of the protein from −2.4 for wild type DENV-4 to 2.0 for variant DENV-4 v3, based on the mean hydrophobicity score for the region encompassing residues 172-176. Neither of these substitutions in E conferred growth advantage of DENV-4 in mosquito or mammalian cells in vitro.

Structural and functional analyses of the E protein indicate that E domain III is responsible for binding to putative receptor(s) on the cell surface and domain II is responsible for viral fusion with the cell membranes (Modis, Y. et al. 2004 *Nature* 427:313-9; Nybakken, G. E. et al. 2005 *Nature* 437:764-9; Rey, F. A. et al. 1995. *Nature* 375:291-8). The epitopes detected by subtype/type specific TBEV-neutralizing MAb i2 and MAb IC3 have been localized to positions 171 and 181 (corresponding to DENV-4 positions 170 and 180) in domain I, respectively (Holzmann, H. Et al. 1997 *J Gen Virol* 78 (Pt 1):31-7; Mandl, C. W. et al. 1989 *J Virol* 63:564-71). An antigenic variant of TBEV that has diminished reactivity with MAb $IC_3$ shows a significant loss of mouse neuroinvasiveness, but its growth phenotype in cultured cells appears not to be affected (Holzmann, H. Et al. 1997 *J Gen Virol* 78 (Pt 1):31-7). MAb i2, which is reactive to domain I of TBEV, has been shown to inhibit virus-induced fusion (Guirakhoo, F. et al. 1991 *J Gen Virol* 72 (Pt 6):1323-9). Dengue virus cross-reactive Mab 4G2 selected a DENV-2 escape mutant that contained substitutions at Ser169 (domain I) and at Glu275 (domain II) (Serafin, I. L. et al. 2001 Arch Virol 146:2469-79). The DENV-2 escape mutant had an altered fusion activity, but the responsible mutation was not precisely assigned. Only a relatively few mouse MAbs that are non-neutralizing mapped to epitopes in domain I of DENV by competitive binding assay (Roehrig, J. T. et al. 1998 *Virology* 246:317-28).

The binding affinity of IgG 5H2 ΔD to each of the two DENV-4 antigenic variants was reduced, indicating that antibody binding was directly responsible for viral neutralization. The in vitro neutralization experiment showed that IgG 5H2 ΔD neutralized DENV-4 before and after adsorption to the cell surface equally efficiently. Thus, viral attachment to the cell surface was apparently not affected by antibody binding. One interpretation is that the antibody probably blocks viral infectivity by preventing viral entry or subsequent membrane fusion. Since mutations of amino acids that are positioned in the interface between domain I and II structures affect the threshold pH for fusion, it has been proposed that both domains change orientation during a conformational shift enabling fusion (Bressanelli, S. et al. 2004 *Embo J* 23:728-38; Modis, Y. et al. 2004 *Nature* 427:313-9). Binding of IgG 5H2 ΔD to domain I on the virus surface could interfere with such structural re-organization, thus preventing fusion from occurring. The chimpanzee DENV-4-neutralizing MAb represents the first antibody reactive to a domain I epitope on DENV E. The epitope probably plays an important role in eliciting strong DENV type-specific immunity in humans. Inclusion of this epitope is an important consideration for an effective vaccine.

The protective efficacy of IgG 5H2 ΔD was evaluated using the mouse dengue encephalitis model described previously (Kaufman, B. M. et al. 1987 *Am J Trop Med Hyg* 36:427-34; Schlesinger, W. et al. 1952 *Am J Trop Med Hyg* 1:66-77). Passive transfer of IgG 5H2 ΔD at approximately 20 μg/mouse afforded 50% protection against challenge with 25 $LD_{50}$ of mouse neurovirulent DENV-4 strain H241. This protective concentration was higher than the 2-4 μg/mouse observed with the most highly neutralizing murine monoclonal antibodies against Japanese encephalitis virus or yellow fever virus (Beasley, D. W. et al. 2004 *Vaccine* 22:3722-6; Kimura-Kuroda, J. 1988 *J Immunol* 141:3606-10; Schlesinger, J. J. et al. 1986 *J Virol* 60:1153-5). However, the strain and age of mice and the virus challenge dose used in each case were also different. To demonstrate proof of concept for protection, the virus challenge dose of DENV-4 was selected to be at 100 $MD_{50}$ (10 ffu) per monkey. The result showed that monkeys that received 2 mg/kg of IgG 5H2 ΔD were completely protected, as indicated by the absence of viremia and lack of sero-conversion. To our knowledge, the current study is the first to evaluate protection of primates against dengue infection by passive transfer of antibody.

In the monkey model, the virus challenge dose may be critical in assessing the protective capacity of antibody. Our results showed that the monkey $MID_{50}$ dose of DENV-4 strain 814669 was about 0.1 ffu. By comparison, monkey $MID_{50}$ values obtained earlier were 22 mosquito infectious $dose_{50}$ (approximately 0.09 pfu) for DENV-4H-241 and 9.5 mosquito infectious $dose_s$) (approximately 0.01 pfu) for DENV-2 PR-159 (Kraiselburd, E. et al. 1985 *Trans R Soc Trop Med Hyg* 79:248-51), 0.5 pfu for DENV-4 strain 341750 Carib and 2×10⁴ pfu for its derived attenuated vaccine (Halstead, S. B. et al. 2003 *Am J Trop Med Hyg* 69:5-11; Marchette, N. J. et al. 1990 *Am J Trop Med Hyg* 43:212-8). Conceivably, the infectivity of dengue viruses depends on the serotype and passage history. An early study showed that as little as one mouse $LD_{50}$ of DENV-1 could infect a human being (Sabin, A. B. 1952 *Am J Trop Med Hyg* 1:30-50). Others also have found that the human $MID_{50}$ of candidate vaccine DENV-4 delta 30 was 0.1 pfu (Durbin, A. P. et al. 2005 *J Infect Dis* 191:710-8). In nature the virus titer transmitted in a mosquito bite could vary widely, depending on mosquito species, extrinsic incubation period (in insects), etc. The amount of dengue virus orally transmitted by *A. albopictus* was measured at between $10^2$ and $10^4$ mosquito infectious $dose_{50}$ (Gubler, D. J. et al. 1976 *Am J Trop Med Hyg* 25:146-50). Protection was not observed in monkeys passively transferred with 0.9 mg/kg of IgG 5H2 AD and challenged with $10^6$ $MID_{50}$ of DENV-4. The information obtained from this study is valuable for future determination of the protective efficacy of the antibody.

Significantly, wild type DENV-4 was not recovered from viremic samples, indicating that IgG 5H2 ΔD prevented spread of the virus in infected monkeys. One antigenic variant contained the Glu-to-$Lys_{174}$ substitution identical to that found in vitro. Molecular epidemiologic analysis of a large number of DENV-4 strains recovered from humans has demonstrated the presence of three genotypes (genotypes I, II, and III) (Klungthong, C. et al. 2004 *Virology* 329:168-79).

DENV-4 strains belonging to the smallest Genotype III group were isolated in Bangkok, Thailand during 1997-2001. Remarkably, all five members contained the Glu-to-Lys$_{174}$. At least four of these genotype III viruses were all recovered from DHF patients with various degrees of severity of diseases, undergoing secondary infections. The presence of Lys$_{174}$-Glu substitution might be significant to allow replication, especially in a DEN4-immune background. It is not known whether an immunological selection pressure was involved in the appearance and disappearance of this particular genotype. There is evidence that DENV-4 strains undergo a continual evolutionary change at a rate as high as $1 \times 10^{-3}$ nucleotide substitutions per site per year (Klungthong, C. et al. 2004 *Virology* 329:168-79). The Lys$_{174}$-Glu mutation has not been identified among members of DENV-4 genotypes I and II, the latter of which represents the most prevalent genotype in the Americas and some part of Asia. Fortunately, the DENV-4 genotype III viruses have thus far remained localized, although their evolutionary course remains uncertain.

ADE has been proposed as an underlying mechanism of severe dengue associated with re-infection by a different dengue virus serotype (Halstead, S. B. 1970 *Yale J Biol Med* 42:350-62). Enhancement of dengue virus replication by antibody can be readily demonstrated using Fc-bearing monocytic cells in vitro and in vivo (Halstead, S. B. et al. 1977 *Nature* 265:739-41; Littaua, R. et al. 1990 *J Immunol* 144: 3183-6). ADE of dengue virus infection can be ready demonstrated with cross-reactive IgG 1A5 in vitro and in monkeys. A direct link between ADE and severe dengue illness is still lacking and the pathogenesis of such illness remains to be elucidated. Type-specific full-length IgG 5H2 also showed ADE activity, albeit at a low level. There remains a concern about the safety of immunization against dengue by passive antibody transfer. Fortunately, introduction of the 9 amino acid deletion in the antibody Fc region ablates the ADE activity of DENV-4 replication in vitro entirely (Goncalvez, A. P. et al. 2007 *Proc Natl Acad Sci USA* 104:9422-27). It is likely that IgG 5H2 ΔD would not mediate ADE of dengue virus infection in vivo. These results warrant further development of the antibody transfer strategy for use in prevention and/or treatment of dengue infections. Before this goal can be realized, the effects of alterations in the Fc region on antibody stability and effector cell functions that play a role in viral clearance will need to be further characterized.

The example below describes in greater detail some of the materials and methods used in Example 3.

EXAMPLE 4

DENV-4 and Cells

Two DENV-4 stocks, designated as DENV-4 (FRhL) and DENV-4 (C6/36), were used for selection of antigenic variants. DENV-4 (C6/36) was recovered from RNA-transfected C6/36 cells and amplified once in the same cells (Lai, C. J. et al. 1991 *Proc Natl. Acad Sci USA* 88:5139-43). DENV-4 (FRhL) was prepared by passage three times in FRhL cells, starting from virus recovered from RNA-transfected C6/36 cells. The full-length DNA clone of DENV-4 (C6/36) contained an XhoI site introduced near the 3' end of the E gene as a genetic marker. This Xho I site was absent in DENV-4 (FRhL). Mosquito C6/36 cells were grown in minimal essential medium (MEM) supplemented with 10% fetal bovine serum (FBS) and antibiotics. Simian Vero cells and FRhL cells were also grown in MEM plus 10% FBS and antibiotics. Human erythroleukemic K562 cells were propagated in Iscove medium. Media were purchased from Invitrogen.

Antibodies

Humanized antibody IgG 5H2 and its variant IgG 5H2 ΔD containing a 9 amino-acid deletion in the Fc region were used (Men, R. et al. 2004 *J Virol* 78:4665-74) (Goncalvez, A. P. et al. 2007 *Proc Natl Acad Sci USA* 104:9422-27). IgG 5H2 ΔD was produced from a clone of Chinese hamster ovary (CHO) cells selected for high level expression as described previously. Briefly, the CHO cells were adapted to grow in suspension culture in a low serum medium. IgG 5H2 ΔD was purified from the medium by affinity binding on a protein A column (Kemp Biotechnology, Gaithersburg, Md.). IgG 5H2 was produced by transient transfection of E 293 cells with expression plasmid (Kemp Biotechnology, Gaithersburg, Md.). Mouse MAb 1H10, specific to DENV-4 E and MAb 1G6 specific to DENV-4 NS1, were kindly given by R Putnak (Walter Reed Army Institute of Research). DENV-4-specific hyperimmune mouse ascites fluid (HMAF) was purchased from American Type Culture Collection (Manassas, Va.). Anti-His (C-term) antibody, coupled to alkaline phosphatase, was purchased from Invitrogen.

Selection of Antigenic Variants

Selection of antigenic variants was performed by partial neutralization of DENV-4 in the presence of Fab 5H2 followed by infection of Vero cells. Approximately $1 \times 10^5$ focus-forming units (ffu) of parental DENV-4 (C6/36) or DENV-4 (FRhL) were mixed with 8 μg of Fab 5H2 in 0.1 ml MEM plus 2% FBS and incubated at 37 C for 1 h. The mixture was added to a monolayer of Vero cells in a T$_{25}$ flask for adsorption at 37 C for 1 h. After removal of excess inoculum, the infected cells were added with Fab 5H2 at 16 μg/ml in 5 ml of MEM plus 2% FBS and incubated at 37 for 7 days. This was repeated for second and third round neutralization and infection of Vero cells. DENV-4 resistant to Fab 5H2 neutralization appeared after the third round of neutralization. Variants were plaque-purified 3 times on Vero cells and amplified in C6/36 cells. The growth properties of DENV-4 antigenic variants and their parental viruses were analyzed by infecting C6/36 cells or Vero cells at a multiplicity of infection (moi) of 0.1 and determining the viral yield at various time points.

Plaque Reduction Neutralization Test (PRNT)

Approximately 50 focus-forming units (ffu) of DENV-4 was mixed with 10-fold serial dilutions of Fab 5H2 or IgG 5H2 ΔD in 0.2 ml and incubated at 37 C for 30 min. The mixture was added to Vero cell monolayers in a 24-well plate in duplicate, adsorbed for 30 min and overlaid with MEM containing 1% gum tragacanth (Sigma). Four days after infection, viral plaques that formed on the cell monolayer were developed by immuno-staining as described (Men, R. et al. 2004 *J Virol* 78:4665-74).

Binding Affinity of Fab 5H2 or IgG 5H2 ΔD

Measurement of the binding affinity (Kd) of Fab 5H2 or IgG 5H2 ΔD to DENV-4 or its derived variants was performed using equilibrium ELISA. Mab 1H10 was used for capturing parental DENV-4 and antigenic variants in order to normalize the virus concentration based on similar optical density readings in an ELISA. Fab 5H2 or IgG1 5H2 ΔD, in serial dilution, was added to react with virus captured with Mab 1H10 on the plate. Equilibrium affinity constants were calculated as the antibody concentration that gave 50% maximum binding.

DNA Sequence Analysis

Viral RNA from each parental DENV-4 and their derived antigenic variants was extracted using Trizol LS Reagent (Invitrogen). Reverse transcription of viral RNA was performed using a complementary sequence in the NS1 region as primer to generate cDNA. The C-prM-E DNA fragment was amplified by PCR and sequence analysis was performed using primers spanning the region in an ABI sequencer (Applied Biosystems).

Analysis of Neutralization and ADE In Vitro

Neutralization of DENV-4 before or after adsorption to Vero cells was performed using a constant amount of virus and dilutions of IgG 5H2 ΔD essentially as described (Crill, W. D. et al. 2001 *J Virol* 75:7769-73). For ADE assay, serial dilutions of full-length IgG 5H2 were mixed with constant amount of parental DENV-4 or an antigenic variant and incubated for 1 h at 37 C. The mixture was added to an equal volume (0.1 ml) of $4 \times 10^5$ K562 cells in Iscove medium plus 2% FBS and incubated for 1.5 h at 37 C. Cells were collected by centrifugation, rinsed, and transferred to a 24-well plate for further incubation for 2 days at 37 C. Percent infected cells was determined by flow cytometry (Goncalvez, A. P. et al. 2007 *Proc Natl Acad Sci USA* 104:9422-27).

Mouse Protection Studies

Groups of three- to four-day-old Balb/c mice were inoculated with IgG 5H2 ΔD by the intra-peritoneal route at a dose of 4, 20, and 92 µg in 50 µl per mouse and mice in the control received only diluent phosphate-buffered saline (PBS). One day later, mice were challenged with a 25 $LD_{50}$ dose (135 ffu) of neurovirulent DENV-4H241 in 30 µl by the intracerebral route. Infected mice were observed for signs of encephalitis and death during a three-week period.

Passive Immunization of Rhesus Monkeys with IgG 5H2 ΔD Against DENV-4 Challenge

Adult rhesus monkeys, sero-negative for dengue virus, were inoculated in the saphenous vein with humanized IgG 5H2 AD in phosphate buffered saline (PBS) at the indicated dose. The control monkeys received PBS diluent only. Twenty-four hr later, monkeys were injected subcutaneously (sc) in the upper back shoulder area with DENV-4 at a dose specified in each study. Diluent of the challenge virus was MEM plus 0.25% human serum albumin. Following DENV-4 challenge, monkeys were bled daily (up to 12 days) for assay of viremia and then bled bi-weekly from the femoral vein for assay of antibody. The experiment was terminated 8 weeks after challenge.

Analysis of Viremia and Sero-Response

For assay of focus-forming units of DENV-4 in serum, freshly-thawed monkey serum samples (0.1 ml) were mixed with 0.1 ml of MEM and the mixture was added directly to a confluent Vero cell monolayer in a 24-well plate. The cell monolayer was stained for dengue virus-infected foci four days later as described (36). Quantitative RT-PCR (TaqMan) was also used to detect dengue virus genome copy numbers in the serum samples (26). Analysis of serum antibodies was carried out by PRNT or by radio-immunoprecipitation (RIP) followed by gel electrophoresis. Mouse MAb1G6 was used in parallel to identify the NS1 immune precipitate.

The following example addresses the effect of the 9-amino acid deletion in the antibody Fc region on the functional activity and stability of MAb 5H2 in chimpanzees.

EXAMPLE 5

Monoclonal antibodies with a 9-amino acid deletion in the Fc region can be used in the prevention of dengue and other flavivirus infections. Humanized monoclonal antibody (MAb) 5H2 containing a 9-amino acid deletion in the Fc, thereafter termed 5H2 ΔD, and its full-length 5H2 neutralized dengue virus type 4 (DENV-4) equally efficiently in vitro. The protective capacity of 5H2 ΔD against DENV-4 in vivo was also explored. The results showed that passive transfer of 5H2 ΔD at 20 µg/mouse afforded 50% protection of suckling mice against challenge with 25 50% lethal dose of mouse neurovirulent DENV-4 strain H241. Passive transfer of antibody to monkeys was also conducted to demonstrate proof of concept for protection against DENV challenge. Monkeys that received 2 mg/kg body weight of 5H2 ΔD were completely protected against 100 50% monkey infectious dose of DENV-4 as indicated by the absence of viremia and sero-conversion (Lai, C. J. et al. 2007 *J Virol* 81: 12766-12774).

The effect of the 9-amino acid deletion in the antibody Fc region on the functional activity and stability of MAb 5H2 in chimpanzees was investigated. The metabolism of IgG differs from those of the other classes of immunoglobulins, in that IgG has the longest survival time in the circulation and the lowest fractional catabolic rate (Waldmann, T. A. et al. 1969 *Prog Allergy* 13:1-110). Earlier pharmacokinetic studies indicated that most plasma proteins, including IgG, were catabolized in close contact with the vascular space, which led to the hypothesis that the catabolic site for the IgG and other proteins was most likely the vascular endothelium (Waldmann, T. A. et al. 1969 *Prog Allergy* 13:1-110). IgG elimination is likely dominated by affinity for the neonatal Fc receptor (FcRn), and the nature of and affinity for the specific target of the antibody (Ghetie, V. et al. 2002 *Immunol Res* 25:97-113; Lobo, E. D. et al. 2004 *J Pharm Sci* 93:2645-68). FcRn plays a critical role in the transfer of maternal IgG to the fetus or neonate, and it is the homeostatic receptor responsible for extending the serum half-life of IgG in adults. FcRn-Fc-co-crystal structure revealed that FcRn binds to the $C_H2$-$C_H3$ hinge region of IgG antibodies (Martin, W. L. et al. 2001 *Cell* 7:867-77), at a site that is distinct from the binding sites of the classical Fcγ R's or the C1q component of complement. ΔD mutation is not close to the FcRn binding site responsible for the maintenance of IgG half-lives; however, other factors may contribute to the rate of the antibody elimination, including the immunogenicity of the antibody (Kuus-Reichel, K. et al. *Clin Diagn Lab Immunol* 1:365-72), the degree and nature of the glycosylation of antibody (Newkirk, M. M. et al. 1996 *Clin Exp Immunol* 106:259-64) and the antibody susceptibility to proteolysis (Gillies, S. D. et al. 2002 *Clin Cancer Res* 8:210-6).

Pharmacokinetics in Chimpanzees

Figure 10:
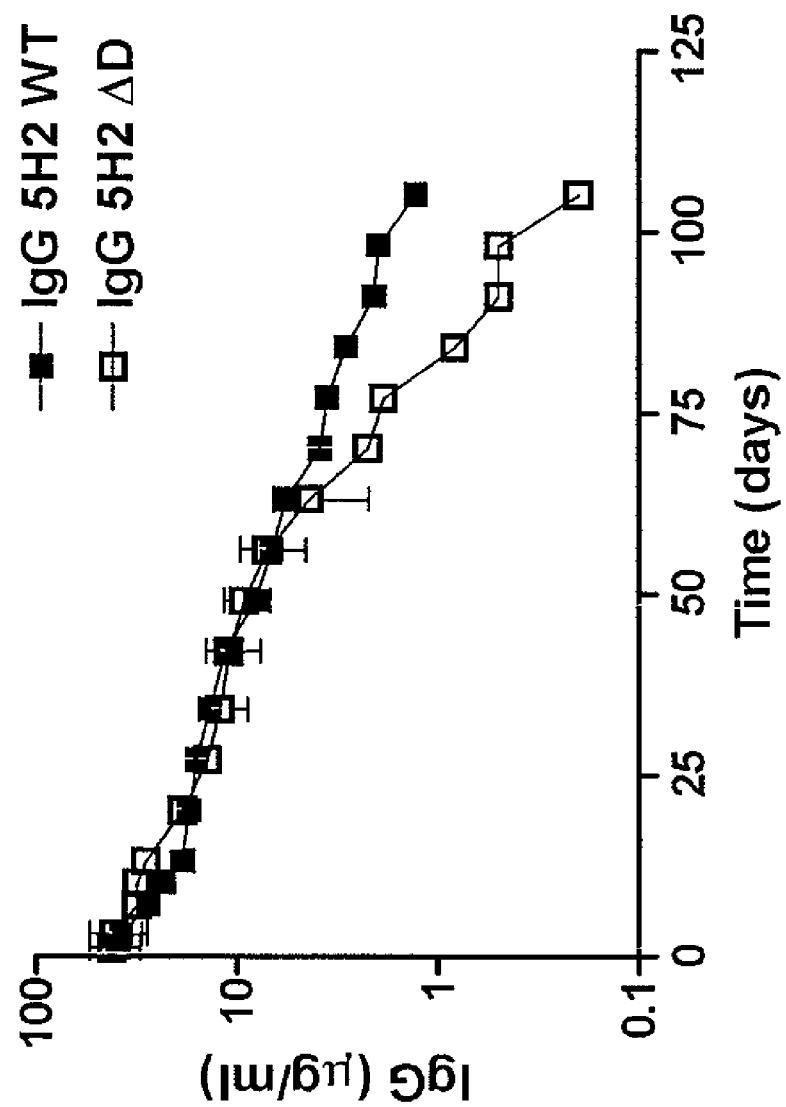
FIG. 10. Plasma concentrations of antibodies IgG 5H2 WT and IgG 5H2 ΔD over time in chimpanzee receiving 1 dose of 5 mg/kg. Symbols and bars show the mean standard deviation antibody concentrations of three independent experiments.

The effect of the Fc mutation ΔD on the pharmacokinetics of IgG 5H2 in chimpanzees was investigated. Two chimpanzees were infused intravenously with full-length IgG 5H2, also termed WT, or IgG 5H2 ΔD (5 mg/kg). Serum samples were collected 24 h prior antibody administration, and various time points over 105 days of post-treatment. Serum samples were analyzed by ELISA and PRNT test to determine the antibody concentration at specified time points. The concentration of each antibody in serum 24 h after infusion was 35.3 µg/ml for IgG 5H2 WT, and 38.5 µg/ml for IgG 5H2 ΔD. The chimpanzee that received either IgG 5H2 WT or IgG 5H2 ΔD demonstrated prolonged antibody serum clearance. The elimination half-life for IgG 5H2 WT was 14.9 days, and for IgG 5H2 ΔD was 18.1 days (FIG. 10), which corresponds to previously reported half-life data of 15-20 days for the clearance of human IgG1 in humans.

Neutralization Studies

Generally, neutralization mediated by antibodies blocks viral attachment and/or membrane fusion events. Neutralizing antibodies can also exert anti-viral effects mediated by the Fc part of the antibody in vivo via processes such as complement activation and antibody-dependent cellular cytotoxicity (ADCC) (Burton, D. R. 2002 *Nat Rev Immunol* 2:706-13; Nimmerjahn, F. et al. 2008 *Nat Rev Immunol* 8:34-47). The antibody Fc region is responsible for complement and Fcγ Receptor binding and deletions in the Fc could alter antibody-mediated effector functions.

Figure 11:
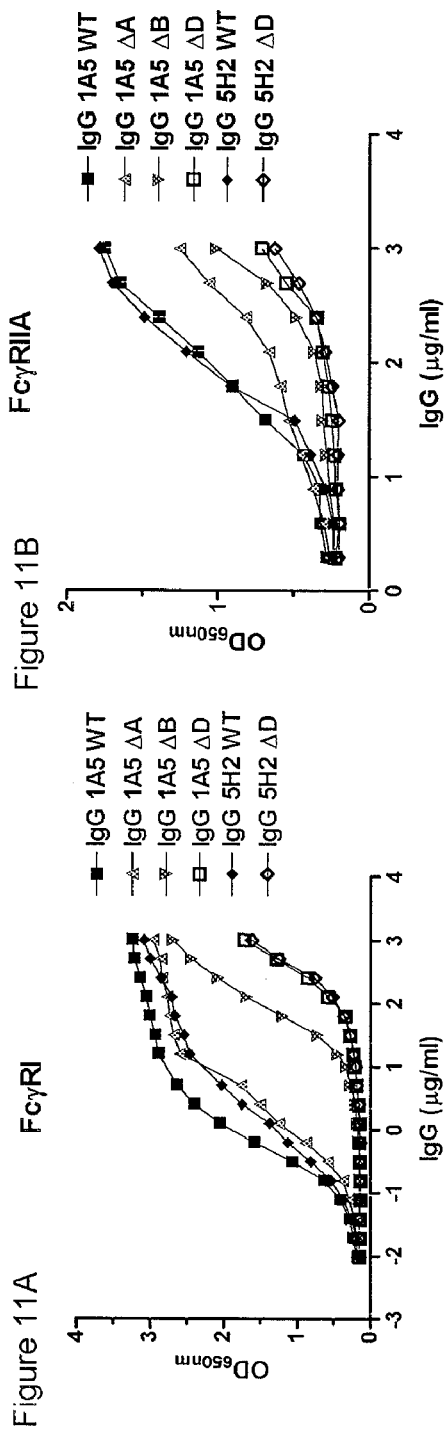
FIG. 11. Interaction of IgG 1A5, IgG 5H2 and variants with Fcγ Receptor molecules. Binding of antibodies to (A) human Fcγ R I, (B) Fcγ R IIA, (C) Fcγ R IIB and (D) Fcγ R IIIB. The variants show weak or no binding to human Fcγ R's.
Figure 11:
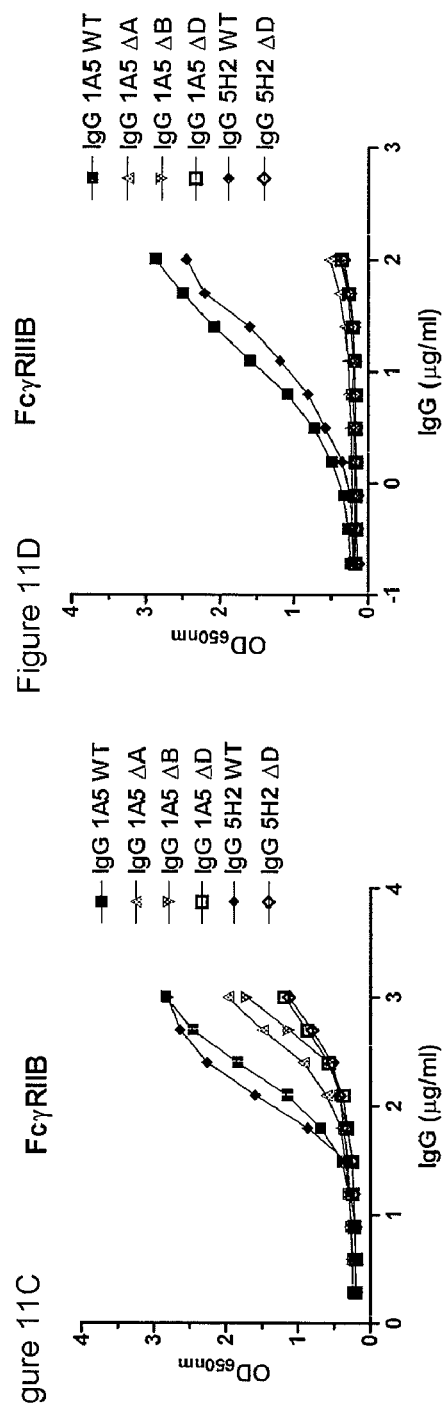
Figure 12:
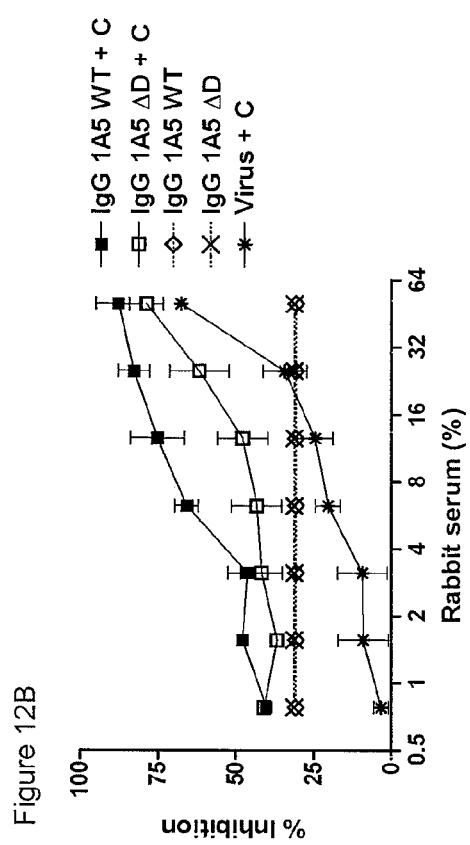
FIG. 12. (A) Interaction of IgG 1A5, IgG 5H2 and variants with purified human C1q. Wild Type IgGs bind C1q. IgG variants show not C1q binding. (B) Complement-mediated neutralization of DENV-4 virions. Increasing concentrations of rabbit complement was pre-incubated with DENV-4 virions (30 min at 37° C.) in the presence or absence of MAbs against the DENV-4 E (IgG 1A5 WT and variant ΔD) prior to addition to a monolayer of Vero cells. After addition of an overlay and 72-h incubation, focus were scored visually. The data shown are from three experiments.
Figure 12:
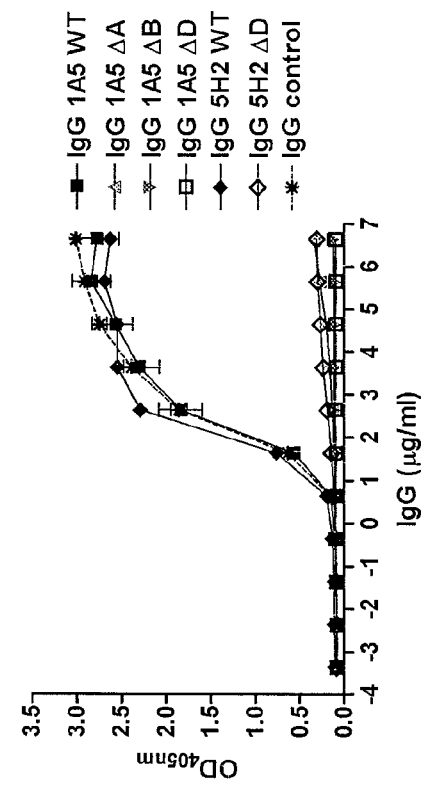

Experiments were performed to explore the abilities of the variant ΔD to interact with human effector-triggering molecules in vitro. Human Fcγ RI, Fcγ RII and Fcγ RIII as well C1q binding were tested for binding to full-length IgGs 1A5 and 5H2 and its deletion variants in an ELISA assay. The binding of the ΔD variants to these effector molecules was significantly reduced (FIGS. 11 and 12A). Thus, the abrogation of ADE of DENV replication in vitro might be associated to the reduction of AD variant binding to the monocyte and macrophage Fcγ R's.

Complement-mediated neutralization of DENV-4 in vitro was also performed. Increasing concentrations of rabbit complement were pre-incubated with DENV-4 virions (30 min at 37° C.) in the presence or absence of MAbs against the DENV-4 E (IgG 1A5 WT and variant ΔD) prior to addition to a monolayer of Vero cells (FIG. 12B). In the absence of antibodies, a dose-dependent reduction in viral plaques was observed. In the presence of IgG 1A5 WT or its variant ΔD, neutralization was enhanced. However, the inhibition of DENV-4 infection was consistently lower with IgG 1A5 ΔD than with IgG 1A5 WT, at different concentrations of rabbit complement. These studies provide important information for the design of antibodies to be used in prophylactic as well as therapeutic strategies against DENV infections.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated peptide of SEQ ID NO: 51 or SEQ ID NO: 52, wherein said peptide comprises a deletion of APELLG-GPS (SEQ ID NO: 16), wherein said peptide binds an Fc gamma receptor (FcγR) with lower affinity to the FcγR than a peptide comprising SEQ ID NO:53 or 54.

2. The isolated peptide of claim 1, wherein said peptide has about 100 fold lower affinity to the FcγR than the peptide comprising SEQ ID NO: 53 or 54.

3. The isolated peptide of claim 1, wherein the peptide is SEQ ID NO: 51.

4. An isolated antibody comprising SEQ ID NO:53 or 54 having a deletion of APELLGGPS (SEQ ID NO: 16), wherein the antibody binds Dengue virus.

5. An isolated nucleic acid encoding the peptide of claim 1.

6. A vector comprising a nucleic acid encoding the peptide of claim 1.

7. An isolated host cell comprising the vector of claim 6.

8. A method for treating dengue-4 virus infection or a symptom thereof in a mammal comprising administering a therapeutically effective amount of the antibody of claim 4.

9. The method of claim 8, further comprising identifying a mammal in need of an agent that treats dengue-4 virus infection or a symptom thereof.

10. The method of claim 9, wherein said identification is clinical evaluation or evaluation by diagnostic approach.

11. A method of reducing antibody-dependent enhancement (ADE) of dengue-4 virus in a mammal comprising administering to said mammal the antibody of claim 4.

12. The method of claim 11, further comprising identifying a mammal in need of an agent that reduces ADE of dengue-4 virus.

13. A method of inducing a complement-mediated neutralization of dengue-4 virus in a mammal comprising administering to said mammal the antibody of claim 4.

14. The method of claim 13, further comprising identifying a mammal in need of an agent that induces complement-mediated neutralization of dengue-4 virus.

15. A composition comprising the peptide of claim 1.

16. A composition comprising the antibody of claim 4.

* * * * *

SEQUENCE LISTING

```
<160> NUMBER OF SEQ ID NOS: 58

<210> SEQ ID NO 1
<211> LENGTH: 4
<212> TYPE: PRT
<213> ORGANISM: Artificial Sequence
<220> FEATURE:
<223> OTHER INFORMATION: Fc region partial sequence

<400> SEQUENCE: 1

Leu Leu Gly Gly
 1

<210> SEQ ID NO 2
<211> LENGTH: 5
<212> TYPE: PRT
<213> ORGANISM: Artificial Sequence
<220> FEATURE:
<223> OTHER INFORMATION: Fc region partial sequence

<400> SEQUENCE: 2

Glu Leu Leu Gly Gly
 1               5

<210> SEQ ID NO 3
<211> LENGTH: 5
<212> TYPE: PRT
<213> ORGANISM: Artificial Sequence
<220> FEATURE:
<223> OTHER INFORMATION: Fc region partial sequence

<400> SEQUENCE: 3

Leu Leu Gly Gly Pro
 1               5

<210> SEQ ID NO 4
<211> LENGTH: 6
<212> TYPE: PRT
<213> ORGANISM: Artificial Sequence
<220> FEATURE:
<223> OTHER INFORMATION: Fc region partial sequence

<400> SEQUENCE: 4

Pro Glu Leu Leu Gly Gly
 1               5
```

-continued

```
<210> SEQ ID NO 5
<211> LENGTH: 6
<212> TYPE: PRT
<213> ORGANISM: Artificial Sequence
<220> FEATURE:
<223> OTHER INFORMATION: Fc region partial sequence

<400> SEQUENCE: 5

Glu Leu Leu Gly Gly Pro
 1               5

<210> SEQ ID NO 6
<211> LENGTH: 6
<212> TYPE: PRT
<213> ORGANISM: Artificial Sequence
<220> FEATURE:
<223> OTHER INFORMATION: Fc region partial sequence

<400> SEQUENCE: 6

Leu Leu Gly Gly Pro Ser
 1               5

<210> SEQ ID NO 7
<211> LENGTH: 7
<212> TYPE: PRT
<213> ORGANISM: Artificial Sequence
<220> FEATURE:
<223> OTHER INFORMATION: Fc region partial sequence

<400> SEQUENCE: 7

Ala Pro Glu Leu Leu Gly Gly
 1               5

<210> SEQ ID NO 8
<211> LENGTH: 7
<212> TYPE: PRT
<213> ORGANISM: Artificial Sequence
<220> FEATURE:
<223> OTHER INFORMATION: Fc region partial sequence

<400> SEQUENCE: 8

Pro Glu Leu Leu Gly Gly Pro
 1               5

<210> SEQ ID NO 9
<211> LENGTH: 7
<212> TYPE: PRT
<213> ORGANISM: Artificial Sequence
<220> FEATURE:
<223> OTHER INFORMATION: Fc region partial sequence

<400> SEQUENCE: 9

Glu Leu Leu Gly Gly Pro Ser
 1               5

<210> SEQ ID NO 10
<211> LENGTH: 7
<212> TYPE: PRT
<213> ORGANISM: Artificial Sequence
<220> FEATURE:
<223> OTHER INFORMATION: Fc region partial sequence

<400> SEQUENCE: 10

Leu Leu Gly Gly Pro Ser Val
 1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Fc region partial sequence

<400> SEQUENCE: 11

Pro Ala Pro Glu Leu Leu Gly Gly
 1               5

<210> SEQ ID NO 12
<211> LENGTH: 8
<212> TYPE: PRT
<213> ORGANISM: Artificial Sequence
<220> FEATURE:
<223> OTHER INFORMATION: Fc region partial sequence

<400> SEQUENCE: 12

Ala Pro Glu Leu Leu Gly Gly Pro
 1               5

<210> SEQ ID NO 13
<211> LENGTH: 8
<212> TYPE: PRT
<213> ORGANISM: Artificial Sequence
<220> FEATURE:
<223> OTHER INFORMATION: Fc region partial sequence

<400> SEQUENCE: 13

Pro Glu Leu Leu Gly Gly Pro Ser
 1               5

<210> SEQ ID NO 14
<211> LENGTH: 8
<212> TYPE: PRT
<213> ORGANISM: Artificial Sequence
<220> FEATURE:
<223> OTHER INFORMATION: Fc region partial sequence

<400> SEQUENCE: 14

Glu Leu Leu Gly Gly Pro Ser Val
 1               5

<210> SEQ ID NO 15
<211> LENGTH: 9
<212> TYPE: PRT
<213> ORGANISM: Artificial Sequence
<220> FEATURE:
<223> OTHER INFORMATION: Fc region partial sequence

<400> SEQUENCE: 15

Pro Ala Pro Glu Leu Leu Gly Gly Pro
 1               5

<210> SEQ ID NO 16
<211> LENGTH: 9
<212> TYPE: PRT
<213> ORGANISM: Artificial Sequence
<220> FEATURE:
<223> OTHER INFORMATION: Fc region partial sequence

<400> SEQUENCE: 16

Ala Pro Glu Leu Leu Gly Gly Pro Ser
 1               5
```

```
<210> SEQ ID NO 17
<211> LENGTH: 9
<212> TYPE: PRT
<213> ORGANISM: Artificial Sequence
<220> FEATURE:
<223> OTHER INFORMATION: Fc region partial sequence

<400> SEQUENCE: 17

Pro Glu Leu Leu Gly Gly Pro Ser Val
 1               5

<210> SEQ ID NO 18
<211> LENGTH: 10
<212> TYPE: PRT
<213> ORGANISM: Artificial Sequence
<220> FEATURE:
<223> OTHER INFORMATION: Fc region partial sequence

<400> SEQUENCE: 18

Pro Ala Pro Glu Leu Leu Gly Gly Pro Ser
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Fc region partial sequence

<400> SEQUENCE: 19

Ala Pro Glu Leu Leu Gly Gly Pro Ser Val
 1               5                  10

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ctcttggcag gatttatggc tta                                            23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
caaagaagac agttcgctgg att                                            23

<210> SEQ ID NO 22
<211> LENGTH: 16
<212> TYPE: DNA
<213> ORGANISM: Artificial Sequence
<220> FEATURE:
<223> OTHER INFORMATION: Probe

<400> SEQUENCE: 22
atgattgggc aaacag                                                    16

<210> SEQ ID NO 23
<211> LENGTH: 9
<212> TYPE: DNA
<213> ORGANISM: Artificial Sequence
```

```
<220> FEATURE:
<223> OTHER INFORMATION: IgG 1A5 Delta B substituted sequence

<400> SEQUENCE: 23 accggtcgc                                                                    9

<210> SEQ ID NO 24
<211> LENGTH: 12
<212> TYPE: DNA
<213> ORGANISM: Artificial Sequence
<220> FEATURE:
<223> OTHER INFORMATION: IgG 1A5 partial sequence

<400> SEQUENCE: 24
tgaactcctg gg                                                               12

<210> SEQ ID NO 25
<211> LENGTH: 6
<212> TYPE: DNA
<213> ORGANISM: Artificial Sequence
<220> FEATURE:
<223> OTHER INFORMATION: AgeI site

<400> SEQUENCE: 25 accggt                                                                       6

<210> SEQ ID NO 26
<211> LENGTH: 22
<212> TYPE: DNA
<213> ORGANISM: Artificial Sequence
<220> FEATURE:
<223> OTHER INFORMATION: Anti-sense primer

<400> SEQUENCE: 26
tttacccgga gacagggaga gg                                                    22

<210> SEQ ID NO 27
<211> LENGTH: 22
<212> TYPE: PRT
<213> ORGANISM: Artificial Sequence
<220> FEATURE:
<223> OTHER INFORMATION: IgG1 1A5 partial sequence

<400> SEQUENCE: 27

Cys Pro Pro Cys Pro Ala Pro Glu Leu Leu Gly Gly Pro Ser Val Phe
 1               5                  10                  15

Leu Phe Pro Pro Lys Pro
            20

<210> SEQ ID NO 28
<211> LENGTH: 22
<212> TYPE: PRT
<213> ORGANISM: Artificial Sequence
<220> FEATURE:
<223> OTHER INFORMATION: IgG1 AF237583 partial sequence

<400> SEQUENCE: 28

Cys Pro Pro Cys Pro Ala Pro Glu Leu Leu Gly Gly Pro Ser Val Phe
 1               5                  10                  15

Leu Phe Pro Pro Lys Pro
            20

<210> SEQ ID NO 29
<211> LENGTH: 21
<212> TYPE: PRT
<213> ORGANISM: Artificial Sequence
```

-continued

```
<220> FEATURE:
<223> OTHER INFORMATION: IgG2 AH013417 partial sequence

<400> SEQUENCE: 29

Cys Pro Pro Cys Pro Ala Pro Pro Val Ala Gly Pro Ser Val Phe Leu
1               5                   10                  15

Phe Pro Pro Lys Pro
            20

<210> SEQ ID NO 30
<211> LENGTH: 21
<212> TYPE: PRT
<213> ORGANISM: Artificial Sequence
<220> FEATURE:
<223> OTHER INFORMATION: IgG2 AY372690 partial sequence

<400> SEQUENCE: 30

Cys Pro Pro Cys Pro Ala Pro Pro Val Ala Gly Pro Ser Val Phe Leu
1               5                   10                  15

Phe Pro Pro Lys Pro
            20

<210> SEQ ID NO 31
<211> LENGTH: 22
<212> TYPE: PRT
<213> ORGANISM: Artificial Sequence
<220> FEATURE:
<223> OTHER INFORMATION: IgG3 AJ390253 partial sequence

<400> SEQUENCE: 31

Cys Pro Arg Cys Pro Ala Pro Glu Leu Leu Gly Gly Pro Ser Val Phe
1               5                   10                  15

Leu Phe Pro Pro Lys Pro
            20

<210> SEQ ID NO 32
<211> LENGTH: 22
<212> TYPE: PRT
<213> ORGANISM: Artificial Sequence
<220> FEATURE:
<223> OTHER INFORMATION: IgG3 AJ390265 partial sequence

<400> SEQUENCE: 32

Cys Pro Arg Cys Pro Ala Pro Glu Leu Leu Gly Gly Pro Ser Val Phe
1               5                   10                  15

Leu Phe Pro Pro Lys Pro
            20

<210> SEQ ID NO 33
<211> LENGTH: 22
<212> TYPE: PRT
<213> ORGANISM: Artificial Sequence
<220> FEATURE:
<223> OTHER INFORMATION: IgG4 AF237586 partial sequence

<400> SEQUENCE: 33

Cys Pro Ser Cys Pro Ala Pro Glu Phe Leu Gly Gly Pro Ser Val Phe
1               5                   10                  15

Leu Phe Pro Pro Lys Pro
            20

<210> SEQ ID NO 34
<211> LENGTH: 34
<212> TYPE: PRT
<213> ORGANISM: Artificial Sequence
```

<220> FEATURE:
<223> OTHER INFORMATION: IgG 1A5 WT partial sequence

<400> SEQUENCE: 34

Cys Pro Pro Cys Pro Ala Pro Glu Leu Leu Gly Gly Pro Ser Val Phe
1               5                   10                  15

Leu Phe Pro Lys Val Ser Asn Lys Ala Leu Pro Ala Pro Ile Glu Lys
            20                  25                  30

Thr Ile

<210> SEQ ID NO 35
<211> LENGTH: 34
<212> TYPE: PRT
<213> ORGANISM: Artificial Sequence
<220> FEATURE:
<223> OTHER INFORMATION: IgG 1A5  A partial sequence

<400> SEQUENCE: 35

Cys Pro Pro Cys Pro Ala Pro Glu Leu Leu Gly Gly Pro Ser Val Phe
1               5                   10                  15

Leu Phe Pro Lys Val Ser Asn Lys Gly Leu Pro Ser Ser Ile Glu Lys
            20                  25                  30

Thr Ile

<210> SEQ ID NO 36
<211> LENGTH: 33
<212> TYPE: PRT
<213> ORGANISM: Artificial Sequence
<220> FEATURE:
<223> OTHER INFORMATION: IgG 1A5  B partial sequence

<400> SEQUENCE: 36

Cys Pro Pro Cys Pro Ala Pro Val Glu Gly Pro Ser Val Phe Leu
1               5                   10                  15

Phe Pro Lys Val Ser Asn Lys Ala Leu Pro Ala Pro Ile Glu Lys Thr
            20                  25                  30

Ile

<210> SEQ ID NO 37
<211> LENGTH: 33
<212> TYPE: PRT
<213> ORGANISM: Artificial Sequence
<220> FEATURE:
<223> OTHER INFORMATION: IgG 1A5  C partial sequence

<400> SEQUENCE: 37

Cys Pro Pro Cys Pro Ala Pro Val Glu Gly Pro Ser Val Phe Leu
1               5                   10                  15

Phe Pro Lys Val Ser Asn Lys Gly Leu Pro Ser Ser Ile Glu Lys Thr
            20                  25                  30

Ile

<210> SEQ ID NO 38
<211> LENGTH: 25
<212> TYPE: PRT
<213> ORGANISM: Artificial Sequence
<220> FEATURE:
<223> OTHER INFORMATION: IgG 1A5  D partial sequence

```
<400> SEQUENCE: 38

Cys Pro Pro Cys Pro Val Phe Leu Phe Pro Lys Val Ser Asn Lys Ala
1               5                   10                  15

Leu Pro Ala Pro Ile Glu Lys Thr Ile
            20                  25

<210> SEQ ID NO 39
<211> LENGTH: 81
<212> TYPE: DNA
<213> ORGANISM: Artificial Sequence
<220> FEATURE:
<223> OTHER INFORMATION: IgG 1A5 WT partial sequence

<400> SEQUENCE: 39
tgtccaccgt gcccaggtaa gccagccctc tcttcctcag cacctgaact cctgggggga      60
ccgtcagtct tcctcttccc c                                                81

<210> SEQ ID NO 40
<211> LENGTH: 81
<212> TYPE: DNA
<213> ORGANISM: Artificial Sequence
<220> FEATURE:
<223> OTHER INFORMATION: IgG 5H2  D partial sequence

<400> SEQUENCE: 40
tgtccaccgt gcccaggtaa gccagccctc tcttcctcgg cacctgaact cctgggggga      60
ccgtcagtct tcctcttccc c                                                81

<210> SEQ ID NO 41
<211> LENGTH: 18
<212> TYPE: PRT
<213> ORGANISM: Artificial Sequence
<220> FEATURE:
<223> OTHER INFORMATION: DENV-4 wt partial sequence

<400> SEQUENCE: 41

Ser Pro Ser Val Glu Val Lys Leu Pro Asp Tyr Gly Glu Leu Thr Leu
1               5                   10                  15

Asp Cys

<210> SEQ ID NO 42
<211> LENGTH: 18
<212> TYPE: PRT
<213> ORGANISM: Artificial Sequence
<220> FEATURE:
<223> OTHER INFORMATION: DENV-4 v3 partial sequence

<400> SEQUENCE: 42

Ser Pro Ser Val Glu Val Glu Leu Pro Asp Tyr Gly Glu Leu Thr Leu
1               5                   10                  15

Asp Cys

<210> SEQ ID NO 43
<211> LENGTH: 18
<212> TYPE: PRT
<213> ORGANISM: Artificial Sequence
<220> FEATURE:
<223> OTHER INFORMATION: DENV-4 v4 partial sequence

<400> SEQUENCE: 43

Ser Pro Ser Val Glu Val Lys Leu Leu Asp Tyr Gly Glu Leu Thr Leu
1               5                   10                  15

Asp Cys
```

```
<210> SEQ ID NO 44
<211> LENGTH: 18
<212> TYPE: PRT
<213> ORGANISM: Artificial Sequence
<220> FEATURE:
<223> OTHER INFORMATION: DENV-3 partial sequence

<400> SEQUENCE: 44

Ala Ser Thr Ala Glu Ala Ile Leu Pro Glu Tyr Gly Thr Leu Gly Leu
1 5 10 15

Glu Cys

<210> SEQ ID NO 45
<211> LENGTH: 18
<212> TYPE: PRT
<213> ORGANISM: Artificial Sequence
<220> FEATURE:
<223> OTHER INFORMATION: DENV-2 partial sequence

<400> SEQUENCE: 45

Ser Ser Ile Thr Glu Ala Glu Leu Thr Gly Tyr Gly Thr Val Thr Met
1 5 10 15

Glu Cys

<210> SEQ ID NO 46
<211> LENGTH: 18
<212> TYPE: PRT
<213> ORGANISM: Artificial Sequence
<220> FEATURE:
<223> OTHER INFORMATION: DENV-1 partial sequence

<400> SEQUENCE: 46

Ala Pro Thr Ser Glu Ile Gln Leu Thr Asp Tyr Gly Ala Leu Thr Leu
1 5 10 15

Asp Cys

<210> SEQ ID NO 47
<211> LENGTH: 18
<212> TYPE: PRT
<213> ORGANISM: Artificial Sequence
<220> FEATURE:
<223> OTHER INFORMATION: JEV partial sequence

<400> SEQUENCE: 47

Ala Pro Ser Ile Thr Leu Lys Leu Gly Asp Tyr Gly Glu Val Thr Leu
1 5 10 15

Asp Cys

<210> SEQ ID NO 48
<211> LENGTH: 18
<212> TYPE: PRT
<213> ORGANISM: Artificial Sequence
<220> FEATURE:
<223> OTHER INFORMATION: WNV partial sequence

<400> SEQUENCE: 48

Ala Pro Ser Tyr Thr Leu Lys Leu Gly Asp Tyr Gly Glu Val Thr Leu
1 5 10 15

Asp Cys

<210> SEQ ID NO 49
<211> LENGTH: 18
<212> TYPE: PRT
<213> ORGANISM: Artificial Sequence

```
<220> FEATURE:
<223> OTHER INFORMATION: TBEV partial sequence

<400> SEQUENCE: 49

Ser Glu Lys Thr

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 52
<211> LENGTH: 330
<212> TYPE: PRT
<213> ORGANISM: Artificial Sequence
<220> FEATURE:
<223> OTHER INFORMATION: IgG 5H2 WT Heavy Chain Fc Region

<400> SEQUENCE: 52

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asp His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 53
<211> LENGTH: 452
<212> TYPE: PRT
<213> ORGANISM: Artificial Sequence
<220> FEATURE:
<223> OTHER INFORMATION: IgG 1A5 WT Heavy Chain

<400> SEQUENCE: 53

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Ile Ser Asp Asn
            20                  25                  30

Val Met His Trp Val Arg Gln Ala Pro Gly Lys Gly Leu Glu Trp Val
        35                  40                  45

Ala Leu Ile Tyr Ser Ala Asp Thr Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asp Ser Leu Arg Pro Glu Asp Thr Ala Val Tyr Tyr Cys Ala
                85                  90                  95

Arg Glu Tyr Cys Thr Gly Asp Thr Cys Phe Ala His Phe Asp Tyr Trp
            100                 105                 110

Gly Gln Gly Thr Leu Val Ser Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asp
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 54
<211> LENGTH: 453
<212> TYPE: PRT
<213> ORGANISM: Artificial Sequence
<220> FEATURE:
<223> OTHER INFORMATION: IgG 5H2 WT Heavy Chain

<400> SEQUENCE: 54

Glu Val Gln Leu Leu Glu Ser Gly Pro Gly Leu Val Lys Pro Ser Glu
  1               5                  10                  15

Thr Leu Ser Leu Thr Cys Thr Val Ser Gly Gly Ser Ile Ser Asp Phe
             20                  25                  30

Tyr Trp Ser Trp Leu Arg Gln Ser Pro Gly Lys Gly Leu Glu Trp Ile
         35                  40                  45

Gly Tyr Ala His Ser Arg Val Ser Ala Tyr Tyr Asn Pro Ser Leu Lys
 50                  55                  60

Ser Arg Val Thr Ile Ser Val Asp Thr Ser Lys Asn Gln Leu Ser Leu
65                  70                  75                  80

Arg Leu Ser Ala Val Thr Ala Ala Asp Thr Ala Leu Tyr Tyr Cys Ala
                85                  90                  95

Arg Gln Gly Thr Gly Thr Thr Gly Val Ser Glu Asp Phe Phe Asp Leu
            100                 105                 110

Trp Gly Gln Gly Thr Lys Val Ile Val Ser Leu Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asp His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                    325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                    405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 55
<211> LENGTH: 110
<212> TYPE: PRT
<213> ORGANISM: Artificial Sequence
<220> FEATURE:
<223> OTHER INFORMATION: IgG 1A5 WT CH2 domain

<400> SEQUENCE: 55

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

-continued

```
<210> SEQ ID NO 56
<211> LENGTH: 110
<212> TYPE: PRT
<213> ORGANISM: Artificial Sequence
<220> FEATURE:
<223> OTHER INFORMATION: IgG 5H2 WT  CH2 domain

<400> SEQUENCE: 56

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 57
<211> LENGTH: 209
<212> TYPE: PRT
<213> ORGANISM: Artificial Sequence
<220> FEATURE:
<223> OTHER INFORMATION: IgG 1A5 WT Light Chain

<400> SEQUENCE: 57

Glu Leu Gln Met Thr Gln Ser Pro Ser Ser Val Ser Ala Ser Val Gly
 1               5                  10                  15

Asp Thr Val Thr Ile Ala Cys Arg Ala Ser Gln Ser Ile Thr Asn Tyr
            20                  25                  30

Leu Ser Trp Tyr Gln Gln Lys Pro Gly Lys Ala Pro Lys Leu Leu Ile
        35                  40                  45

Tyr His Ala Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys His Tyr Gly Tyr Gly Thr His Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Asn Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn
```

```
<210> SEQ ID NO 58
<211> LENGTH: 210
<212> TYPE: PRT
<213> ORGANISM: Artificial Sequence
<220> FEATURE:
<223> OTHER INFORMATION: IgG 5H2 WT Light Chain

<400> SEQUENCE: 58

Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ile Arg
             20                  25                  30

Leu Asn Trp Tyr Gln Gln Lys Pro Gly Lys Ala Pro Lys Leu Leu Ile
         35                  40                  45

Tyr Asp Ala Ser Thr Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Asn Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210
```